United States Patent
Bielke et al.

(10) Patent No.: US 10,716,840 B2
(45) Date of Patent: Jul. 21, 2020

(54) COMPOSITIONS AND METHODS OF ENHANCING IMMUNE RESPONSES TO ENTERIC PATHOGENS

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US)

(72) Inventors: Lisa Bielke, Wooster, OH (US); Sherryll Layton, Rogers, AR (US); Billy Hargis, Fayetteville, AR (US); Neil R. Pumford, Bentonville, AR (US); Olivia B. Faulkner, Shawnee, KS (US); Luc Berghman, College Station, TX (US); Daad Abi-Ghanem, Tigard, OR (US)

(73) Assignees: THE BOARD OF TRUSTEES OF THE UNIVERSITY OF ARKANSAS, Little Rock, AR (US); THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 16/531,893

(22) Filed: Aug. 5, 2019

(65) Prior Publication Data

US 2019/0351042 A1 Nov. 21, 2019

Related U.S. Application Data

(63) Continuation of application No. 14/776,986, filed as application No. PCT/US2014/027416 on Mar. 14, 2014, now Pat. No. 10,376,571.

(60) Provisional application No. 61/790,301, filed on Mar. 15, 2013.

(51) Int. Cl.
| | | |
|---|---|---|
| C07H 21/02 | (2006.01) | |
| A61K 39/00 | (2006.01) | |
| A61K 39/02 | (2006.01) | |
| A61K 39/112 | (2006.01) | |
| A61K 39/108 | (2006.01) | |
| C07K 16/12 | (2006.01) | |
| C12N 15/85 | (2006.01) | |

(52) U.S. Cl.
CPC ...... A61K 39/0275 (2013.01); A61K 39/0258 (2013.01); A61K 39/105 (2013.01); A61K 39/107 (2013.01); C07K 16/1232 (2013.01); C12N 15/85 (2013.01); *A61K 2039/523* (2013.01); *A61K 2039/53* (2013.01); *C07K 2317/34* (2013.01); *Y02A 50/474* (2018.01); *Y02A 50/482* (2018.01)

(58) Field of Classification Search
CPC ................. A61K 39/00; A61K 39/02

USPC .............. 536/23.1, 23.7; 424/9.1, 9.2, 184.1, 424/185.1, 234.1

See application file for complete search history.

(56) References Cited

U.S. PATENT DOCUMENTS

| | | |
|---|---|---|
| 5,683,700 A | 11/1997 | Charles et al. |
| 5,747,309 A | 5/1998 | Allan et al. |
| 5,961,974 A | 10/1999 | Armitage et al. |
| 5,962,406 A | 10/1999 | Armitage et al. |
| 5,981,724 A | 11/1999 | Armitage et al. |
| 6,087,329 A | 7/2000 | Armitage et al. |
| 6,190,669 B1 | 2/2001 | Noriega et al. |
| 6,264,951 B1 | 7/2001 | Armitage et al. |
| 6,306,387 B1 | 10/2001 | Galan |
| 6,410,711 B1 | 6/2002 | Armitage et al. |
| 6,479,258 B1 | 11/2002 | Short |
| 6,713,279 B1 | 3/2004 | Short |
| 6,902,906 B1 | 6/2005 | Chatfield |
| 6,923,957 B2 | 8/2005 | Lowery et al. |
| 6,923,958 B2 | 8/2005 | Xiang et al. |
| 6,936,425 B1 | 8/2005 | Hensel et al. |
| 6,969,609 B1 | 11/2005 | Schlom et al. |
| 7,087,573 B1 | 8/2006 | Lazarus et al. |
| 7,118,751 B1 | 10/2006 | Ledbetter et al. |
| 7,238,499 B2 | 7/2007 | Reddy |
| 7,332,298 B2 | 2/2008 | Kornbluth |
| 7,371,392 B2 | 5/2008 | Tripp et al. |
| 7,405,270 B2 | 7/2008 | Armitage et al. |
| 7,495,090 B2 | 2/2009 | Prussak et al. |
| 7,842,501 B2 | 11/2010 | Cai et al. |
| 7,928,213 B2 | 4/2011 | Prussak et al. |
| 8,604,178 B2 | 12/2013 | Bottje et al. |
| 8,956,618 B2 | 2/2015 | Berghman et al. |

(Continued)

FOREIGN PATENT DOCUMENTS

| | | |
|---|---|---|
| WO | WO 1993/008207 | 4/1993 |
| WO | WO 1995/014487 | 6/1995 |

(Continued)

OTHER PUBLICATIONS

Agterberg, M. et al., "Outer membrane protein PhoE as a carrier for the exposure of foreign antigenic determinants at the bacterial cell surface," Antonie Van Leeuwenhoek (1991) 59(4):249-262.

(Continued)

*Primary Examiner* — Rodney P Swartz
(74) *Attorney, Agent, or Firm* — Quarles & Brady LLP

(57) ABSTRACT

Vaccine vectors capable of eliciting an immune response to enteric bacteria and methods of using the same are provided. The vaccine vectors include a polynucleotide encoding a PAL polypeptide. The PAL polypeptide may be expressed on the surface of the vaccine vector. The vaccine vector may also include a second polypeptide encoding an immunostimulatory polypeptide such as a CD154 polypeptide or an HMGB1 polypeptide.

19 Claims, 7 Drawing Sheets

Specification includes a Sequence Listing.

(56) References Cited

U.S. PATENT DOCUMENTS

| | | |
|---|---|---|
| 8,956,849 B2 | 2/2015 | Bottje et al. |
| 8,961,990 B2 | 2/2015 | Hargis et al. |
| 9,125,854 B2 | 9/2015 | Bottje et al. |
| 9,226,957 B2 | 1/2016 | Bottje et al. |
| 9,603,915 B2 | 3/2017 | Barta et al. |
| 9,884,099 B2 | 2/2018 | Barta et al. |
| 9,913,893 B2 | 3/2018 | Berghman et al. |
| 10,004,798 B2 | 6/2018 | Bottje et al. |
| 10,016,493 B2 | 7/2018 | Bottje et al. |
| 10,328,137 B2 | 6/2019 | Barta et al. |
| 2001/0021386 A1 | 9/2001 | Nuijten et al. |
| 2003/0045492 A1 | 3/2003 | Tang et al. |
| 2003/0165538 A1 | 9/2003 | Goldman et al. |
| 2004/0006006 A9 | 1/2004 | Armitage et al. |
| 2004/0047873 A1 | 3/2004 | Al-Shamkhani et al. |
| 2004/0053841 A1 | 3/2004 | Tracey et al. |
| 2004/0141948 A1 | 7/2004 | O'Keefe |
| 2004/0156851 A1 | 8/2004 | Newman |
| 2004/0203039 A1 | 10/2004 | Hensel et al. |
| 2005/0181994 A1 | 8/2005 | Chamberlain et al. |
| 2005/0226888 A1 | 10/2005 | Deisseroth et al. |
| 2006/0014248 A1 | 1/2006 | Marshall et al. |
| 2006/0078994 A1 | 4/2006 | Healey et al. |
| 2006/0121047 A1 | 6/2006 | Tracey |
| 2006/0233829 A1 | 10/2006 | Curtiss |
| 2006/0286074 A1 | 12/2006 | Tang et al. |
| 2007/0025982 A1 | 2/2007 | Ledbetter et al. |
| 2007/0082400 A1 | 4/2007 | Healey et al. |
| 2007/0128183 A1 | 6/2007 | Meinke et al. |
| 2007/0128223 A1 | 6/2007 | Tang et al. |
| 2007/0237779 A1 | 10/2007 | Ledbetter et al. |
| 2007/0249553 A1 | 10/2007 | Newell et al. |
| 2008/0004207 A1 | 1/2008 | Tsung et al. |
| 2008/0075728 A1 | 3/2008 | Newman |
| 2008/0124320 A1 | 5/2008 | O'Keefe |
| 2008/0305120 A1 | 12/2008 | Messmer et al. |
| 2009/0004194 A1 | 1/2009 | Kedl |
| 2009/0324644 A1 | 12/2009 | Ramos et al. |
| 2010/0040608 A1 | 2/2010 | Wahren-Herlenius et al. |
| 2010/0047231 A1 | 2/2010 | Zabaleta Azpiroz et al. |
| 2010/0112002 A1 | 5/2010 | Lien et al. |
| 2010/0166788 A1 | 7/2010 | Scorza et al. |
| 2010/0233152 A1 | 9/2010 | Bullerdiek |
| 2010/0291109 A1 | 11/2010 | Kedl |
| 2010/0292309 A1 | 11/2010 | Vile et al. |
| 2011/0020318 A1 | 1/2011 | Tracey et al. |
| 2011/0027309 A1 | 2/2011 | Bottje et al. |
| 2012/0282291 A1 | 11/2012 | Berghman et al. |
| 2015/0150958 A1 | 6/2015 | Pillich et al. |
| 2015/0297714 A1 | 10/2015 | Hargis et al. |
| 2017/0143823 A1 | 5/2017 | Hargis et al. |
| 2018/0333474 A1 | 11/2018 | Bottje et al. |

FOREIGN PATENT DOCUMENTS

| | | |
|---|---|---|
| WO | WO 1996/026735 | 9/1996 |
| WO | WO 1996/040918 | 12/1996 |
| WO | WO 1999/027948 | 6/1999 |
| WO | WO 1999/032138 | 7/1999 |
| WO | WO 1999/059609 | 11/1999 |
| WO | WO 2000/063395 | 10/2000 |
| WO | WO 2000/063405 | 10/2000 |
| WO | WO 2001/054472 | 1/2001 |
| WO | WO 2001/013948 | 3/2001 |
| WO | WO 2001/042298 | 6/2001 |
| WO | WO 2001/056602 | 8/2001 |
| WO | WO 2002/036769 | 5/2002 |
| WO | WO 2002/092773 | 11/2002 |
| WO | WO 2003/026691 | 4/2003 |
| WO | WO 2003/099340 | 12/2003 |
| WO | WO 2004/009615 | 1/2004 |
| WO | WO 2004/046338 | 6/2004 |
| WO | WO 2004/046345 | 6/2004 |
| WO | WO 2005/025604 | 3/2005 |
| WO | WO 2005/035570 | 4/2005 |
| WO | WO 2005/049641 | 6/2005 |
| WO | WO 2005/058950 | 6/2005 |
| WO | WO 2005/113598 | 12/2005 |
| WO | WO 2006/012373 | 2/2006 |
| WO | WO 2006/042177 | 4/2006 |
| WO | WO 2006/105972 | 10/2006 |
| WO | WO 2007/011606 | 1/2007 |
| WO | WO 2007/042583 | 4/2007 |
| WO | WO 2007/054658 | 5/2007 |
| WO | WO 2007/056266 | 5/2007 |
| WO | WO 2007/128183 | 6/2007 |
| WO | WO 2007/103048 | 9/2007 |
| WO | WO 2007/117682 | 10/2007 |
| WO | WO 2008/036675 | 3/2008 |
| WO | WO 2008/109825 | 9/2008 |
| WO | WO 2009/059018 | 5/2009 |
| WO | WO 2009/059298 | 5/2009 |
| WO | WO 2011/036564 | 3/2011 |
| WO | WO 2011/091255 | 7/2011 |
| WO | WO 2011/156619 | 12/2011 |
| WO | WO 2013/071298 | 5/2013 |
| WO | WO 2014/028776 | 2/2014 |
| WO | WO 2014/127185 | 8/2014 |

OTHER PUBLICATIONS

Al-Ramadi, B. K. et al., "Induction of innate immunity by IL-2 expressing *Salmonella* confers protection against letal challenge," Mol. Immunol. (2003) 39:763-770.

Al-Ramadi, B. K. et al., "Influence of vector-encoded cytokines on anti-*Salmonella* immunity: divergent effects of interleukin-2 and tumor necrosis factor alpha," Infect. Immun. (2001) 69:3960-3988.

Al-Ramadi, B. K. et al., "CD154 is essential for Protective Immunity in Experimental *Salmonella* Infection: Evidence for a Dual Role in Innate and Adaptive Immune Responses" J Immunol (2006) 176: 496-506.

Andersson, U. et al., "HMGB1 is a therapeutic target for sterile inflammation and infection," Annu. Rev. Immunol. (2011) 29:139-162.

Anonymous. WHO. Fact sheet No. 139. (http://www.who.int/mediacentre/factsheets/fs139/en/). 2005.

Babu, U., et al., "*Salmonella enteritidis* clearance and immune responses in chickens following *Salmonella* vaccination and challenge," Vet. Immunol. Immunopathol. (2004)101:251-257.

Barr, T.A. et al., "A potent adjuvant effect of CD40 antibody attached to antigen," Immunology (2003) 109:87-92.

Barrow, P. A., et al., "Reduction in faecal excretion of *Salmonella typhimurium* strain F98 in chickens vaccinated with live and killed *S. typhimurium* organisms," Epidemiol. Infect. (1990) 104:413-426.

Blomfield, I.C. et al., "Allelic exchange in *Escherichia coli* using the Bacillus subtilis sacB gene and a temperature-sensitive pSC101 replicon," Mol Microbiol (1991) 5(6):1447-1457.

Buckley, A.M. et al., "Evaluation of live-attenuated *Salmonella* vaccines expressing Campylobacter antigens for control of C. jejuni in poultry," (2010) Vaccine 28(4):1094-1105.

Cervantes-Barragán et al., "TLR2 and TLR4 signaling shapes specific antibody responses to *Salmonella typhi* antigens," Eur J Immunol. (2009) 39(1):126-35.

Charbit, A. et al., "Probing the topology of a bacterial membrane protein by genetic insertion of a foreign epitope; expression at the cell surface," EMBO J (1986) 5(11):3029-3037.

Charbit, A. et al., "Versatility of a vector for expressing foreign polypeptides at the surface of gram-negative bacteria," Gene (1988) 70(1):181-189.

Chatfield et al., "The development of oral vaccines based on live attenuated *Salmonella* strains," FEMS Immunol. Med. Microbiol. (1993) 7:1-7.

Cole, K. et al., "Evaluation of a novel recombinant *Salmonella* vaccine vector for avian influenza," Poultry Science (2007) 86(Supp. 1):585-586.

Combet, C. et al., "NPS@: Network Protein Sequence Analysis." Trends in Biochemical Sciences (2000) 25(3): 147-150.

(56) References Cited

OTHER PUBLICATIONS

Cox, M.M. et al., "Scarless and site-directed mutagenesis in *Salmonella enteritidis* chromosome," BMC Biotech. (2007) 7(59):10 pages.
Crawford, J. et al., "Baculovirus-derived hemagglutinin vaccines protect against lethal influenza infections by avian H5 and H7 subtypes," Vaccine (1999) 17:2265-2274.
Database UniProt Accession No. B7MFZ4, "SubName: Full= Peptidoglycan-associated outer membrane lipoprotein," XP002762330, UNIPROT:B7MFZ4 Database accession No. B7MFZ4.
Du, A. et al., "Efficacy of a DNA vaccine delivered in attenuated *Salmonella typhimurium* against Eimeria tenella infection in chickens," International Journal of Parasitology (2005) 35:777-785.
Duc, L.H. et al., "Bacterial Spores as Vaccine Vehicles," Infection and Immunity (2003) 71(5): 2810-2818.
Dumitriu, I.E. et al., "HMGB1: guiding immunity from within," Trends Immunol. (2005) 26(7):381-387.
Ellis, R.W., "New technologies for making vaccines," (1988) Vaccines, Chapter 29:568-574.
Faham, A. et al., "Liposomal Ag engrafted with peptides of sequence derived from HMGB1 induce potent Ag-specific and anti-tumour immunity," (2009) 27(42):5846-5854.
Farnell, M.B. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes: Distinct Response from Naïve and Memory Cells," J Immunol (2003) 171:4621-4629.
Fernandez-Cabezudo et al., "Evidence for the requirement for CD40-CD154 interactions in resistance to infections with attenuated *Salmonella*," J. Endotoxin Res. (2005) 11:395-399.
Fuchs, P. et al., "Targeting recombinant antibodies to the surface of *Escherichia coli*: fusion to a peptidoglycan associated lipoprotein," Nature Biotechnology (1991), 9(12):1369-1372.
Gares, S.L. et al., "Immunotargeting with CD154 (CD40 ligand) enhances DNA vaccine responses in ducks," Clin. Vaccine Immun. (2006) 13:958-965.
Gast, R.K. et al., "The relationship between the magnitude of the specific antibody response to experimental *Salmonella enteritidis* infection in laying hens and their production of contaminated eggs," Avian Diseases (2001) 45:425-431.
GenBank AF178849, "High mobility group protein HMG1 [Gallus gallus]," Sep. 27, 2000.
Godlewska, R., et al., "Peptidoglycan-associated lipoprotein (Pal) of Gram-negative bacteria: function, structure, role in pathogenesis and potential application in immunoprophylaxis," FEMS microbiology letters (2009) 298(1):1-11.
Grangette, C. et al., Protection against tetanus toxin after intragastric administration of two recombinant lactic acid bacteria: Impact and strain viability and in vivo persistence, Vaccine (2002) 20:3304-3309.
Greenspan, N.S. et al., "Defining epitopes: It's not as easy as it seems," Nature Biotechnol. (1999) 17:936-937.
Grewal, I.S. et al., "CD40 and CD154 in cell-mediated immunity," Annu. Rev. Immunology. (1998) 16:111-35.
Gundogdu, O. et al., "Re-annotation and re-analysis of the Campylobacter jejuni NCTC11168 genome sequence," BMC Genomics (2007) 8(162).
Harcourt, J.L. et al., "CD40 ligand (CD154) improves the durability of respiratory syncytial virus DNA vaccination in BALB/c mice," Vaccine (2003) 21(21-22):2964-2979.
Hargis, B, "Live Recombinant *Salmonella* Vaccination with Novel Universal Antigen Presentation and Immune Protection," USDA Grant Project Status, Jan. 14, 2012.
Hargis, B.M. et al., "Reduction of Campylobacter in Poultry by Live Oral-Vectored Vaccine" USDA Grant Project Status, Nov. 2008 https://portal.nifa.usda.gov/web/crisprojectpages/0215105-reduction-of-campylobacter-in-poultry-by-live-oral-vectored-vaccine.html.

Harris, H.E. et al., "Mini-review: The nuclear protein HMGB1 as a proinflammatory mediator," European J. of Immunology (2004) 34:1503-1512.
Hashmi, T. et al., "In silico identification of vaccine coordinates against enteric pathogens by a comparative genome sequence approach," AsPac J. Mol. Biol. Biotechn (2010) 18(3):17-22.
Hayes, L.J. et al., "Chlamydia trachomatis major outer membrane protein epitopes expressed as fusions with LamB in an attenuated aro A strain of *Salmonella typhimurium*; their application as potential immunogens," Journal of General Microbiology (1991) 137:1557-1564.
Hoang, T.H. et al., "Recombinant Bacillus subtilis Expressing the Clostridium perfringens Alpha Toxoid Is a Candidate Orally Delivered Vaccine against Necrotic Enteritis," Infection and Immunity (2008) 76(11): 5257-5265.
Holmgren, J. et al., "Mucosal immunity: implications for vaccine development," Immunobiol. (1992) 184:157-179.
Husseiny, M.L. et al., "Rapid method for the construction of *Salmonella enterica* serovar typhimurium vaccine carrier strains," Infec. Immun (2005) 73(3):1598-1605.
Katz, J.M. et al., "Adjuvant activity of the heat-labile enterotoxin from enterotoxigenic *Escherichia coli* for oral administration of inactivated influenza virus vaccine," J. Infect. Dis. (1997) 175:352-363.
Kimura, R. et al., "Enhancement of antibody response by high mobility group box protein-1-based DNA immunization," J. of Immunol. Methods (2010) 361:21-30.
Koch, F. et al., "High level IL-12 production by murine dendritic cells: upregulation via MHC class II and CD40 molecules and downregulation by IL-4 and IL-10," J. Exp. Med. (1996) 184:741-746.
Kotton, C.N. et al., "Enteric pathogens as vaccine vectors for foreign antigen delivery," Infect. Immun. (2004) 72:5535-5547.
Kwon, Y.M. et al., "*Salmonella*-based vaccines for infectious diseases," Expert Review of Vaccines (2007) 6(2):147-152.
Lavelle, E.C. et al., "Delivery systems and adjuvants for oral vaccines," Expert Opin. Drug Deliv. (2006) 3(6):747-762.
Layton, S.L., et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.
Layton et al., Evaluation of *Salmonella*-vectored Campylobacter peptide epitopes for reduction of Campylobacter jejuni in broiler chickens, Clin. Vaccine Immunol (2011) 18(3):449-454.
Lee, J.S. et al., "Surface-displayed viral antigens on *Salmonella* carrier vaccine," Nat. Biotechnol. (2000) 18:645-648.
Li, W., "Synergistic antibody induction by antigen-CD40 ligand fusion protein as improved immunogen," Immunology (2005) 115(2):215-222.
Lowe, D.C. et al., "Characterization of candidate live oral *Salmonella typhi* vaccine strains harboring defined mutations in aroA, aroC, and htrA," Infection and Immunity (1999) Feb.:700-707.
Mann, J.F. et al., "Delivery systems: a vaccine strategy for overcoming mucosal tolerance?" Expert Rev. Vaccines (2009) 8(1):103-112.
Manoj, S. et al., "Targeting with Bovine CD154 enhances humoral immune responses induced by a DNA vaccine in sheep," (2003) Journal of Immunology 170:989-996.
Mauriello, E.M.F. et al., "Display of heterologous antigens on the Bacillus subtilis spore coat using CotC as a fusion partner," (2004) Vaccine 22(9-10):1177-1187.
McSorley, S.J. et al., "Characterization of CD4+ T cell responses durng natural infection with *Salmonella typhimurium*," (2000) J. of Immunol. 164:986-993.
Mendoza, R.B. et al., "Cutting edge: Immunostimulatory effects of a plasmid expressing CD40 ligand (CD154) on gene immunization," Journal of Immunology (1997) 159(12):5777-5781.
Miga, A. et al., "The role of CD40-CD154 interactions in the regulation of cell mediated immunity," Immunol. Invest. (2000) 29:111-114.
Mogensen, T.H., "Pathogen recognition and inflammatory signaling in innate immune defenses," Clin. Microbiol. Rev. (2009) 22(2):240-273.

(56) References Cited

OTHER PUBLICATIONS

Mohamadzadeh, M. et al., "Targeting mucosal dendritic cells with microbial antigens from probiotic lactic acid bacteria," Expert Rev. Vaccines (2008) 7(2):163-174.

Moyle, P.M. et al., "Mucosal immunisation: adjuvants and delivery systems," Curr. Drug Deliv. (2004) 1(4):385-396.

Muthumani, G. et al., "Co-immunization with an optimized plasmid-encoded immune stimulatory interleukin, high-mobility group box 1 protein, results in enhanced interferon-y secretion by antigen-specific CD8 T cells," Immunology (2009) 128: e612-e620.

Nakajima, A. et al., "Antitumor effect of CD40 ligand: Elicitation of local and systemic antitumor responses by IL-12 and B7," (1998) Journal of Immunology 161:1901-1907.

O'Callaghan, D. et al., "Immunogenicity of foreign peptide epitopes expressed in bacterial envelope proteins," Research in Microbiology (1990) 141:963-969.

Ochoa-Reparaz, J. et al., "Humoral immune reponse in hens naturally infected with *Salmonella enteritidis* against outer membrane proteins and other surface structural antigens," (2004) Vet. Res. 35:291-298.

Pasetti, M. et al., "Animal models paving the way for clinical trials of attenuated *Salmonella enterica* servoar Typhi live oral vaccines and live vectors," Vaccine (2003) 21:401-418.

Pisetsky, D.S. et al., "High-mobility group box protein 1 (HMGB1): an alarmin mediating the pathogenesis of rheumatic disease," Arthritis Res. Ther. (2008) 10(3):209.

Rabsch, W. et al., "Competitive exclusion of *Salmonella enteritidis* by *Salmonella gallinarum* in poultry," Emerging Inf. Diseases (2000) 6(5):443-448.

Rovere-Querini, P. et al., "HMGB1 is an endogenous immune adjuvant released by necrotic cells," EMBO Rep. (2004) 5(8):825-830.

Russmann, H. et al., "Delivery of epitopes by the *Salmonella* type III secretion system for vaccine development," Science (1998) 281(5376):565-568.

Saenz, R. et al., "HMGB1-derived peptide acts as adjuvant inducing immune responses to peptide and protein antigen," (2010) Vaccine 28(47):7556-7562.

Seo, et al., "Mucosal humoral immunity to experimental *Salmonella enteritidis* infection in the chicken crop," Avian Diseases (2002) 46(4):1015-1020; p. 1018 fig 2a.

Sizemore, D.R. et al., "Live, attenuated *Salmonella typhimurium* vectoring Campylobacter antigens," Vaccine (2006) 24(18):3793-3803.

Su, G.F. et al., "Construction of stable LamB-Shiga toxin B subunit hybrids: analysis of expression in *Salmonella typhimurium* aroA strains and stimulation of B subunit-specific mucosal and serum antibody responses," Infect. Immun (1992) 60(8):3345-3359.

Swayne, D.E., "Vaccines for List A poultry diseases: emphasis on avian influenza," Dev. Biol. (2003) 114:201-212.

Tregaskes, C.A. et al., "Conservation of biological properties of the CD40 ligand, CD154 in a non-mammalian vertebrate," Dev. Comp. Immunol. (2005) 29:361-374.

Tükel et al., "CsgA is a pathogen-associated molecular pattern of *Salmonella enterica* serotype Typhimurium that is recognized by Toll-like receptor 2," Mol Microbiol (2005) 58(1):289-304.

Ulloa, L. et al., "High-mobility group box 1 (HMGB1) protein: friend and foe," Cytokine Growth Factor Rev. (2006) 17(3):189-201.

Uyen, N.Q. et al., "Enhanced immunisation and expression strategies using bacterial spores as heat-stable vaccine delivery vehicles," Vaccine (2007) 25 356-365.

Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.

Verjans, G.M. et al., "Intracellular processing and presentation of T cell epitopes, expressed by recombinant *Escherichia coli* and *Salmonella typhimurium*, to human T cells," Eur J Immunol (1995) 25(2):405-410.

Vierira-Pinto, M. et al.., "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52(10):476-81.

Wang, J. et al., "Immunogenicity of viral B-cell epitopes inserted into two surface loops of the *Escherichia coli* K12 LamB protein and expressed in an attenuated aroA strain of *Salmonella typhimurium*," Vaccine (1999) 17(1):1-12.

Wolfenden et al., "Development and evaluation of candidate recombinant *Salmonella*-vectored *Salmonella* vaccines," Poult Sci (2010) 89(11):2370-9.

Wyszynska, A. et al., "Oral immunization of chickens with avirulent *Salmonella* vaccine streain carring C. Jejuni 72Dz/92 cjaA gene elicits specific humoral immune response associated with protection against challenge with wild-type Campylobacter," Vaccine (2004) 22(11-12):1379-1389.

Xu, Y. et al., "The role of CD40-CD154 interaction in cell immunoregulation," J. Biomed. Sci. (2004) 11:426-438.

International Search Report and Written Opinion for International Patent Application No. PCT/US2014/027416 dated Jul. 18, 2014 (11 pages).

Office Action for U.S. Appl. No. 14/776,986 dated Jun. 21, 2016 (30 pages).

Office Action for U.S. Appl. No. 14/776,986 dated Jan. 9, 2017 (9 pages).

Office Action for U.S. Appl. No. 14/776,986 dated Aug. 14, 2017 (13 pages).

Office Action for U.S. Appl. No. 14/776,986 dated Apr. 20, 2018 (11 pages).

Figure 1

Serum IgG Following Vaccination with BS-PAL Construct

Figure 2

Serum sIgA Following Vaccination with BS-PAL Construct

SEQUENCE LISTING

<160> NUMBER OF SEQ ID NOS: 46

<210> SEQ ID NO 1
<211> LENGTH: 19
<212> TYPE: PRT
<213> ORGANISM: E. coli
<220> FEATURE:
<221> NAME/KEY: misc_feature
<222> LOCATION: (1)..(19)
<223> OTHER INFORMATION: PAL bis from E. coli

<400> SEQUENCE: 1

Glu Gly His Ala Asp Glu Arg Gly Thr Pro Glu Tyr Asn Ile Ser Leu
1               5                   10                  15

Gly Glu Arg

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Gly His Ala Asp Glu Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Asp Glu Arg Gly Thr Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Glu Tyr Asn Ile Ser Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ile Ser Leu Gly Glu Arg
1               5

<210> SEQ ID NO 6
<211> LENGTH: 19
<212> TYPE: PRT
<213> ORGANISM: Vibrio spp.
<220> FEATURE:
<221> NAME/KEY: misc_feature
<222> LOCATION: (1)..(19)

<223> OTHER INFORMATION: PAL bis from vibrio spp.

<400> SEQUENCE: 6

Glu Gly His Ala Asp Glu Arg Gly Thr Pro Glu Tyr Asn Ile Ala Leu
1               5                   10                  15

Gly Glu Arg

<210> SEQ ID NO 7
<211> LENGTH: 17
<212> TYPE: PRT
<213> ORGANISM: Campylobacter spp.
<220> FEATURE:
<221> NAME/KEY: misc_feature
<222> LOCATION: (1)..(17)
<223> OTHER INFORMATION: corresponding peptide from Campylobacter spp.

<400> SEQUENCE: 7

Glu Gly Asn Cys Asp Glu Trp Gly Thr Asp Glu Tyr Asn Gln Ala Leu
1               5                   10                  15

Gly

<210> SEQ ID NO 8
<211> LENGTH: 19
<212> TYPE: PRT
<213> ORGANISM: E. coli
<220> FEATURE:
<221> NAME/KEY: misc_feature
<222> LOCATION: (1)..(19)
<223> OTHER INFORMATION: PAL from E. coli

<400> SEQUENCE: 8

Thr Val Glu Gly His Ala Asp Glu Arg Gly Thr Pro Glu Tyr Asn Ile
1               5                   10                  15

Ser Leu Gly

<210> SEQ ID NO 9
<211> LENGTH: 8
<212> TYPE: PRT
<213> ORGANISM: Avian Influenza virus m2e

<400> SEQUENCE: 9

Glu Val Glu Thr Pro Ile Arg Asn
1               5

<210> SEQ ID NO 10
<211> LENGTH: 8
<212> TYPE: PRT
<213> ORGANISM: Avian Influenza virus m2e

<400> SEQUENCE: 10

Glu Val Glu Thr Pro Thr Arg Asn
1               5

<210> SEQ ID NO 11
<211> LENGTH: 12
<212> TYPE: PRT
<213> ORGANISM: Avian Influenza virus
<220> FEATURE:
<221> NAME/KEY: misc_feature
<222> LOCATION: (1)..(12)
<223> OTHER INFORMATION: Avian Influenza virus (HA5 UA)

<400> SEQUENCE: 11

Leu Leu Ser Arg Ile Asn His Phe Glu Lys Ile Gln
1               5                   10

```
<210> SEQ ID NO 12
<211> LENGTH: 19
<212> TYPE: PRT
<213> ORGANISM: Avian Influenza virus
<220> FEATURE:
<221> NAME/KEY: misc_feature
<222> LOCATION: (1)..(19)
<223> OTHER INFORMATION: Avian Influenza virus (HA5 LB)

<400> SEQUENCE: 12

Ala Asn Pro Ala Asn Asp Leu Cys Tyr Pro Gly Asp Phe Asn Asp Tyr
1               5                   10                  15

Glu Glu Leu

<210> SEQ ID NO 13
<211> LENGTH: 16
<212> TYPE: PRT
<213> ORGANISM: Avian Influenza virus
<220> FEATURE:
<221> NAME/KEY: misc_feature
<222> LOCATION: (1)..(16)
<223> OTHER INFORMATION: Avian Influenza virus (NP 54-69)

<400> SEQUENCE: 13

Gly Arg Leu Ile Gln Asn Ser Ile Thr Ile Glu Arg Met Val Leu Ser
1               5                   10                  15

<210> SEQ ID NO 14
<211> LENGTH: 14
<212> TYPE: PRT
<213> ORGANISM: Avian Influenza virus
<220> FEATURE:
<221> NAME/KEY: misc_feature
<222> LOCATION: (1)..(14)
<223> OTHER INFORMATION: Avian Influenza virus (NP 147-160)

<400> SEQUENCE: 14

Thr Tyr Gln Arg Thr Arg Ala Leu Val Arg Thr Gly Met Asp
1               5                   10

<210> SEQ ID NO 15
<211> LENGTH: 190
<212> TYPE: PRT
<213> ORGANISM: Gallus gallus
<220> FEATURE:
<221> NAME/KEY: misc_feature
<222> LOCATION: (1)..(190)
<223> OTHER INFORMATION: Chicken HMGB1 amino acid

<400> SEQUENCE: 15

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
        50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Phe Arg Pro Lys
```

```
                    100                 105                 110
Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp
                180                 185                 190

<210> SEQ ID NO 16
<211> LENGTH: 85
<212> TYPE: PRT
<213> ORGANISM: Artificial Sequence
<220> FEATURE:
<223> OTHER INFORMATION: Synthetic HMGB1 box a1

<400> SEQUENCE: 16

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr
                85

<210> SEQ ID NO 17
<211> LENGTH: 54
<212> TYPE: PRT
<213> ORGANISM: Artificial Sequence
<220> FEATURE:
<223> OTHER INFORMATION: Synthetic HMGB1 box a2

<400> SEQUENCE: 17

Pro Asp Ala Ser Val Asn Phe Ser Glu Phe Ser Lys Lys Cys Ser Glu
1               5                   10                  15

Arg Trp Lys Thr Met Ser Ser Lys Glu Lys Gly Lys Phe Glu Asp Met
            20                  25                  30

Ala Lys Ala Asp Lys Leu Arg Tyr Glu Lys Glu Met Lys Asn Tyr Val
        35                  40                  45

Pro Pro Lys Gly Glu Thr
    50

<210> SEQ ID NO 18
<211> LENGTH: 73
<212> TYPE: PRT
<213> ORGANISM: Artificial Sequence
<220> FEATURE:
<223> OTHER INFORMATION: Synthetic HMGB1 box b1

<400> SEQUENCE: 18

Lys Asp Pro Asn Ala Pro Lys Arg Pro Pro Ser Ala Phe Phe Leu Phe
1               5                   10                  15
```

Cys Ser Glu Phe Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr
65                  70

<210> SEQ ID NO 19
<211> LENGTH: 69
<212> TYPE: PRT
<213> ORGANISM: Artificial Sequence
<220> FEATURE:
<223> OTHER INFORMATION: Synthetic HMGB1 box b2

<400> SEQUENCE: 19

Asn Ala Pro Lys Arg Pro Pro Ser Ala Phe Phe Leu Phe Cys Ser Glu
1               5                   10                  15

Phe Arg Pro Lys Ile Lys Gly Glu His Pro Gly Leu Ser Ile Gly Asp
            20                  25                  30

Val Ala Lys Lys Leu Gly Glu Met Trp Asn Asn Thr Ala Ala Asp Asp
        35                  40                  45

Lys Gln Pro Tyr Glu Lys Lys Ala Ala Lys Leu Lys Glu Lys Tyr Glu
    50                  55                  60

Lys Asp Ile Ala Ala
65

<210> SEQ ID NO 20
<211> LENGTH: 21
<212> TYPE: PRT
<213> ORGANISM: Artificial Sequence
<220> FEATURE:
<223> OTHER INFORMATION: Synthetic HMGB1 RAGE Binding domain

<400> SEQUENCE: 20

Lys Asp Pro Asn Ala Pro Lys Arg Pro Pro Ser Ala Phe Phe Leu Phe
1               5                   10                  15

Cys Ser Glu Phe Arg
            20

<210> SEQ ID NO 21
<211> LENGTH: 33
<212> TYPE: PRT
<213> ORGANISM: Artificial Sequence
<220> FEATURE:
<223> OTHER INFORMATION: Synthetic HMGB1 proinflammatory cytokine
      activity

<400> SEQUENCE: 21

Leu Lys Glu Lys Tyr Glu Lys Asp Ile Ala Ala Tyr Arg Ala Lys Gly
1               5                   10                  15

Lys Val Asp Ala Gly Lys Lys Val Val Ala Lys Ala Glu Lys Ser Lys
            20                  25                  30

Lys

<210> SEQ ID NO 22
<211> LENGTH: 215
<212> TYPE: PRT
<213> ORGANISM: Homo sapiens
<220> FEATURE:

<221> NAME/KEY: misc_feature
<222> LOCATION: (1)..(215)
<223> OTHER INFORMATION: HMGB1

<400> SEQUENCE: 22

| Met | Gly | Lys | Gly | Asp | Pro | Lys | Lys | Pro | Arg | Gly | Lys | Met | Ser | Ser | Tyr |
| 1 | | | | 5 | | | | | 10 | | | | | 15 | |

| Ala | Phe | Phe | Val | Gln | Thr | Cys | Arg | Glu | Glu | His | Lys | Lys | Lys | His | Pro |
| | | | 20 | | | | | 25 | | | | | 30 | | |

| Asp | Ala | Ser | Val | Asn | Phe | Ser | Glu | Phe | Ser | Lys | Lys | Cys | Ser | Glu | Arg |
| | | 35 | | | | | 40 | | | | | 45 | | | |

| Trp | Lys | Thr | Met | Ser | Ala | Lys | Glu | Lys | Gly | Lys | Phe | Glu | Asp | Met | Ala |
| 50 | | | | | 55 | | | | | 60 | | | | | |

| Lys | Ala | Asp | Lys | Ala | Arg | Tyr | Glu | Arg | Glu | Met | Lys | Thr | Tyr | Ile | Pro |
| 65 | | | | | 70 | | | | | 75 | | | | | 80 |

| Pro | Lys | Gly | Glu | Thr | Lys | Lys | Phe | Lys | Asp | Pro | Asn | Ala | Pro | Lys |
| | | | | 85 | | | | | 90 | | | | | 95 |

| Arg | Pro | Pro | Ser | Ala | Phe | Phe | Leu | Phe | Cys | Ser | Glu | Tyr | Arg | Pro | Lys |
| | | | 100 | | | | | 105 | | | | | 110 | | |

| Ile | Lys | Gly | Glu | His | Pro | Gly | Leu | Ser | Ile | Gly | Asp | Val | Ala | Lys | Lys |
| | | | 115 | | | | | 120 | | | | | 125 | | |

| Leu | Gly | Glu | Met | Trp | Asn | Asn | Thr | Ala | Ala | Asp | Asp | Lys | Gln | Pro | Tyr |
| | 130 | | | | | 135 | | | | | 140 | | | | |

| Glu | Lys | Lys | Ala | Ala | Lys | Leu | Lys | Glu | Lys | Tyr | Glu | Lys | Asp | Ile | Ala |
| 145 | | | | | 150 | | | | | 155 | | | | | 160 |

| Ala | Tyr | Arg | Ala | Lys | Gly | Lys | Pro | Asp | Ala | Ala | Lys | Lys | Gly | Val | Val |
| | | | | 165 | | | | | 170 | | | | | 175 | |

| Lys | Ala | Glu | Lys | Ser | Lys | Lys | Lys | Glu | Glu | Glu | Glu | Asp | Glu | Glu |
| | | | 180 | | | | | 185 | | | | | 190 | | |

| Asp | Glu | Glu | Asp | Glu | Glu | Glu | Glu | Asp | Glu | Asp | Glu | Asp | Glu | Asp | Glu |
| | | | 195 | | | | | 200 | | | | | 205 | | |

| Glu | Glu | Asp | Asp | Asp | Asp | Glu |
| | 210 | | | | | 215 |

<210> SEQ ID NO 23
<211> LENGTH: 205
<212> TYPE: PRT
<213> ORGANISM: Danio rerio
<220> FEATURE:
<221> NAME/KEY: misc_feature
<222> LOCATION: (1)..(205)
<223> OTHER INFORMATION: Zebra fish HMGB1

<400> SEQUENCE: 23

| Met | Gly | Lys | Asp | Pro | Thr | Lys | Pro | Arg | Gly | Lys | Met | Ser | Ser | Tyr | Ala |
| 1 | | | | 5 | | | | | 10 | | | | | 15 | |

| Tyr | Phe | Val | Gln | Thr | Cys | Arg | Glu | Glu | His | Lys | Lys | Lys | His | Pro | Glu |
| | | | 20 | | | | | 25 | | | | | 30 | | |

| Ala | Thr | Val | Asn | Phe | Ser | Glu | Phe | Ser | Lys | Lys | Cys | Ser | Glu | Arg | Trp |
| | | 35 | | | | | 40 | | | | | 45 | | | |

| Lys | Thr | Met | Ser | Ala | Lys | Glu | Lys | Gly | Lys | Phe | Glu | Asp | Met | Ala | Lys |
| 50 | | | | | 55 | | | | | 60 | | | | | |

| Leu | Asp | Lys | Ala | Arg | Tyr | Glu | Arg | Glu | Met | Lys | Asn | Tyr | Ile | Pro | Pro |
| 65 | | | | | 70 | | | | | 75 | | | | | 80 |

| Lys | Gly | Glu | Lys | Lys | Lys | Arg | Phe | Lys | Asp | Pro | Asn | Ala | Pro | Lys | Arg |
| | | | | 85 | | | | | 90 | | | | | 95 | |

| Pro | Pro | Ser | Ala | Phe | Phe | Ile | Phe | Cys | Ser | Glu | Phe | Arg | Pro | Lys | Val |

100                 105                 110

Lys Glu Glu Thr Pro Gly Leu Ser Ile Gly Asp Val Ala Lys Arg Leu
            115                 120                 125

Gly Glu Met Trp Asn Lys Ile Ser Ser Glu Glu Lys Gln Pro Tyr Glu
        130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Gly Gly Ala Ala Lys Ala Pro Ser
                165                 170                 175

Lys Pro Asp Lys Ala Asn Asp Glu Asp Glu Asp Asp Glu Glu Glu
            180                 185                 190

Asp Glu Asp Asp Asp Asp Glu Glu Glu Asp Asp Glu
            195                 200                 205

<210> SEQ ID NO 24
<211> LENGTH: 272
<212> TYPE: PRT
<213> ORGANISM: Gallus gallus
<220> FEATURE:
<221> NAME/KEY: misc_feature
<222> LOCATION: (1)..(272)
<223> OTHER INFORMATION: CD154 chicken

<400> SEQUENCE: 24

Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
            20                  25                  30

Val Val Gln Thr Ile Gly Thr Val Leu Phe Cys Leu Tyr Leu His Met
        35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

Met Glu Glu Asp Arg Leu Leu Met Lys Gly Leu Asp Thr His Ser Thr
    210                 215                 220

Ser Thr Ala Leu Cys Glu Leu Gln Ser Ile Arg Glu Gly Gly Val Phe
225                 230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270

<210> SEQ ID NO 25
<211> LENGTH: 261
<212> TYPE: PRT
<213> ORGANISM: Homo sapiens
<220> FEATURE:
<221> NAME/KEY: misc_feature
<222> LOCATION: (1)..(261)
<223> OTHER INFORMATION: Human CD154

<400> SEQUENCE: 25

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 26
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Human CD154 peptide

<400> SEQUENCE: 26

Trp Ala Glu Lys Gly Tyr Tyr Thr Met Ser Asn
1               5                   10

<210> SEQ ID NO 27
<211> LENGTH: 11
<212> TYPE: PRT
<213> ORGANISM: Galus gallus
<220> FEATURE:
<221> NAME/KEY: misc_feature
<222> LOCATION: (1)..(11)
<223> OTHER INFORMATION: Chicken CD154 peptide

<400> SEQUENCE: 27

Trp Met Thr Thr Ser Tyr Ala Pro Thr Ser Ser
1               5                   10

<210> SEQ ID NO 28
<211> LENGTH: 10
<212> TYPE: PRT
<213> ORGANISM: Anas sp.
<220> FEATURE:
<221> NAME/KEY: misc_feature
<222> LOCATION: (1)..(10)
<223> OTHER INFORMATION: Duck CD154 peptide

<400> SEQUENCE: 28

Trp Asn Lys Thr Ser Tyr Ala Pro Met Asn
1               5                   10

<210> SEQ ID NO 29
<211> LENGTH: 10
<212> TYPE: PRT
<213> ORGANISM: Mus sp.
<220> FEATURE:
<221> NAME/KEY: misc_feature
<222> LOCATION: (1)..(10)
<223> OTHER INFORMATION: Mouse CD154 peptide

<400> SEQUENCE: 29

Trp Ala Lys Lys Gly Tyr Tyr Thr Met Lys
1               5                   10

<210> SEQ ID NO 30
<211> LENGTH: 10
<212> TYPE: PRT
<213> ORGANISM: Bos taurus
<220> FEATURE:
<221> NAME/KEY: misc_feature
<222> LOCATION: (1)..(10)
<223> OTHER INFORMATION: Cow CD154 peptide

<400> SEQUENCE: 30

Trp Ala Pro Lys Gly Tyr Tyr Thr Leu Ser
1               5                   10

<210> SEQ ID NO 31
<211> LENGTH: 21
<212> TYPE: PRT
<213> ORGANISM: Campylobacter jejuni Cj0113

<400> SEQUENCE: 31

Gly Val Ser Ile Thr Val Glu Gly Asn Cys Asp Glu Trp Gly Thr Asp
1               5                   10                  15

Glu Tyr Asn Gln Ala
            20

<210> SEQ ID NO 32

```
<211> LENGTH: 19
<212> TYPE: PRT
<213> ORGANISM: Vibrio spp.
<220> FEATURE:
<221> NAME/KEY: misc_feature
<222> LOCATION: (1)..(19)
<223> OTHER INFORMATION: Vibrio spp. alternative PAL epitope

<400> SEQUENCE: 32

Thr Val Glu Gly His Ala Asp Glu Arg Gly Thr Pro Glu Tyr Asn Ile
1               5                   10                  15

Ala Leu Gly

<210> SEQ ID NO 33
<211> LENGTH: 57
<212> TYPE: DNA
<213> ORGANISM: E. coli
<220> FEATURE:
<221> NAME/KEY: misc_feature
<222> LOCATION: (1)..(57)
<223> OTHER INFORMATION: E. coli nucleotide sequence for PAL epitope

<400> SEQUENCE: 33
gaaggtcacg cggacgaacg tggtaccccg gaatacaaca tctctctggg tgaacgt        57

<210> SEQ ID NO 34
<211> LENGTH: 56
<212> TYPE: DNA
<213> ORGANISM: Artificial Sequence
<220> FEATURE:
<223> OTHER INFORMATION: Synthetic nucleotide sequence encoding in
      vector (CJ0113-HMGB1-PAL)

<400> SEQUENCE: 34
gaaggtcacg cggacgaacg tggtaccccg aatacaacat ctctctgggt gaacgt         56

<210> SEQ ID NO 35
<211> LENGTH: 18
<212> TYPE: PRT
<213> ORGANISM: Artificial Sequence
<220> FEATURE:
<223> OTHER INFORMATION: Synthetic peptide sequence encoded by SEQ ID
      NO: 34 mutant PAL

<400> SEQUENCE: 35

Glu Gly His Ala Asp Glu Arg Gly Thr Pro Asn Thr Thr Ser Leu Trp
1               5                   10                  15

Val Asn

<210> SEQ ID NO 36
<211> LENGTH: 9
<212> TYPE: PRT
<213> ORGANISM: E. coli
<220> FEATURE:
<221> NAME/KEY: misc_feature
<222> LOCATION: (1)..(9)
<223> OTHER INFORMATION: Epitope of PAL from E. coli

<400> SEQUENCE: 36

Glu Tyr Asn Ile Ser Leu Gly Glu Arg
1               5

<210> SEQ ID NO 37
<211> LENGTH: 9
<212> TYPE: PRT
<213> ORGANISM: Vibrio spp.
<220> FEATURE:
```

<221> NAME/KEY: misc_feature
<222> LOCATION: (1)..(9)
<223> OTHER INFORMATION: Epitope of PAL from Vibrio spp.

<400> SEQUENCE: 37

Glu Tyr Asn Ile Ala Leu Gly Glu Arg
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Tyr Lys Val Thr Val Glu
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

Thr Val Glu Gly His Ala
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Gly Thr Pro Glu Tyr Asn
1               5

<210> SEQ ID NO 41
<211> LENGTH: 726
<212> TYPE: DNA
<213> ORGANISM: Artificial Sequence
<220> FEATURE:
<223> OTHER INFORMATION: Synthetic insert in CJ0113-PAL-HMGB1 nucleotide

<400> SEQUENCE: 41
tcctcctccg gtgtttctat caccgttgaa ggtaactgcg acgaatgggg taccgacgaa 60
tacaaccagg cgtcctcctc cgaaggtcac gcggacgaac gtggtacccc ggaatacaac 120
atctctctgg gtgaacgttc ctcctccatg ggtaaaggcg acccgaaaaa accgcgtggt 180
aaaatgtctt cttacgcgtt cttcgttcag acctgccgtg aagaacacaa aaaaaaacac 240
ccggacgctt ctgttaactt ctctgaattc tctaaaaaat gctctgaaag atggaaaacc 300
atgtcttcta aagaaaaagg taaattcgaa gacatggcga aagcggacaa actgagatac 360
gaaaaagaaa tgaaaaacta cgttccgccg aaaggtgaaa ccaaaaaaaa attcaaagac 420
ccgaacgcgc cgaaacgtcc gccgtctgcg ttcttcctgt tctgcagcga attcagaccg 480
aaaatcaaag gtgaacaccc gggtctgtct atcggtgacg ttgcgaaaaa actgggtgaa 540
atgtggaaca acaccgcggc ggacgacaaa cagccgtacg aaaaaaaagc ggcgaaactg 600
aaagaaaaat acgaaaaaga catcgcggcg tacagagcga aaggtaaagt tgacgcgggt 660

```
aaaaaagttg ttgcgaaagc ggaaaaatct aaaaaaaaaa aagaagaaga agaagactcc    720
tcctcc                                                              726
```

<210> SEQ ID NO 42
<211> LENGTH: 242
<212> TYPE: PRT
<213> ORGANISM: Artificial Sequence
<220> FEATURE:
<223> OTHER INFORMATION: Synthetic insert in CJ0113-PAL-HMGB1 amino acid

<400> SEQUENCE: 42

```
Ser Ser Ser Gly Val Ser Ile Thr Val Glu Gly Asn Cys Asp Glu Trp
1               5                   10                  15

Gly Thr Asp Glu Tyr Asn Gln Ala Ser Ser Ser Glu Gly His Ala Asp
            20                  25                  30

Glu Arg Gly Thr Pro Glu Tyr Asn Ile Ser Leu Gly Glu Arg Ser Ser
        35                  40                  45

Ser Met Gly Lys Gly Asp Pro Lys Lys Pro Arg Gly Lys Met Ser Ser
    50                  55                  60

Tyr Ala Phe Phe Val Gln Thr Cys Arg Glu Glu His Lys Lys Lys His
65                  70                  75                  80

Pro Asp Ala Ser Val Asn Phe Ser Glu Phe Ser Lys Lys Cys Ser Glu
                85                  90                  95

Arg Trp Lys Thr Met Ser Ser Lys Glu Lys Gly Lys Phe Glu Asp Met
            100                 105                 110

Ala Lys Ala Asp Lys Leu Arg Tyr Glu Lys Glu Met Lys Asn Tyr Val
        115                 120                 125

Pro Pro Lys Gly Glu Thr Lys Lys Lys Phe Lys Asp Pro Asn Ala Pro
    130                 135                 140

Lys Arg Pro Pro Ser Ala Phe Phe Leu Phe Cys Ser Glu Phe Arg Pro
145                 150                 155                 160

Lys Ile Lys Gly Glu His Pro Gly Leu Ser Ile Gly Asp Val Ala Lys
                165                 170                 175

Lys Leu Gly Glu Met Trp Asn Asn Thr Ala Ala Asp Asp Lys Gln Pro
            180                 185                 190

Tyr Glu Lys Lys Ala Ala Lys Leu Lys Glu Lys Tyr Glu Lys Asp Ile
        195                 200                 205

Ala Ala Tyr Arg Ala Lys Gly Lys Val Asp Ala Gly Lys Lys Val Val
    210                 215                 220

Ala Lys Ala Glu Lys Ser Lys Lys Lys Lys Glu Glu Glu Glu Asp Ser
225                 230                 235                 240

Ser Ser
```

<210> SEQ ID NO 43
<211> LENGTH: 726
<212> TYPE: DNA
<213> ORGANISM: Artificial Sequence
<220> FEATURE:
<223> OTHER INFORMATION: Synthetic insert in CJ0113-HMGB1-PAL nucleotide
      CJ0113-HMGB1-PAL

<400> SEQUENCE: 43

```
tcctcctccg gtgtttctat caccgttgaa ggtaactgcg acgaatgggg taccgacgaa    60
tacaaccagg cgtcctcctc catgggtaaa ggcgacccga aaaaccgcg tggtaaaatg    120 tcttcttacg cgttcttcgt tcagacctgc cgtgaagaac acaaaaaaaa acacccggac   180
```

```
gcttctgtta acttctctga attctctaaa aaatgctctg aaagatggaa aaccatgtct      240
tctaaagaaa aaggtaaatt cgaagacatg gcgaaagcgg acaaactgag atacgaaaaa      300
gaaatgaaaa actacgttcc gccgaaaggt gaaaccaaaa aaaaattcaa agacccgaac      360
gcgccgaaac gtccgccgtc tgcgttcttc ctgttctgca gcgaattcag accgaaaatc      420
aaaggtgaac cccgggtct gtctatcggt gacgttgcga aaaaactggg tgaaatgtgg      480
aacaacaccg cggcggacga caaacagccg tacgaaaaaa aagcggcgaa actgaaagaa      540
aaatacgaaa aagacatcgc ggcgtacaga gcgaaaggta agttgacgc gggtaaaaaa      600 gttgttgcga aagcggaaaa atctaaaaaa aaaaagaag aagaagaaga ctcctcctcc      660
gaaggtcacg cggacgaacg tggtaccccg aatacaaca tctctctggg tgaacgttcc      720
tcctcc                                                                 726
```

```
<210> SEQ ID NO 44
<211> LENGTH: 242
<212> TYPE: PRT
<213> ORGANISM: Artificial Sequence
<220> FEATURE:
<223> OTHER INFORMATION: Synthetic insert in CJ0113-HMGB1-PAL amino acid

<400> SEQUENCE: 44

Ser Ser Ser Gly Val Ser Ile Thr Val Glu Gly Asn Cys Asp Glu Trp
1               5                   10                  15

Gly Thr Asp Glu Tyr Asn Gln Ala Ser Ser Met Gly Lys Gly Asp
            20                  25                  30

Pro Lys Lys Pro Arg Gly Lys Met Ser Ser Tyr Ala Phe Phe Val Gln
        35                  40                  45

Thr Cys Arg Glu Glu His Lys Lys Lys His Pro Asp Ala Ser Val Asn
    50                  55                  60

Phe Ser Glu Phe Ser Lys Lys Cys Ser Glu Arg Trp Lys Thr Met Ser
65                  70                  75                  80

Ser Lys Glu Lys Gly Lys Phe Glu Asp Met Ala Lys Ala Asp Lys Leu
                85                  90                  95

Arg Tyr Glu Lys Glu Met Lys Asn Tyr Val Pro Pro Lys Gly Glu Thr
            100                 105                 110

Lys Lys Lys Phe Lys Asp Pro Asn Ala Pro Lys Arg Pro Pro Ser Ala
        115                 120                 125

Phe Phe Leu Phe Cys Ser Glu Phe Arg Pro Lys Ile Lys Gly Glu His
    130                 135                 140

Pro Gly Leu Ser Ile Gly Asp Val Ala Lys Lys Leu Gly Glu Met Trp
145                 150                 155                 160

Asn Asn Thr Ala Ala Asp Asp Lys Gln Pro Tyr Glu Lys Lys Ala Ala
                165                 170                 175

Lys Leu Lys Glu Lys Tyr Glu Lys Asp Ile Ala Ala Tyr Arg Ala Lys
            180                 185                 190

Gly Lys Val Asp Ala Gly Lys Lys Val Val Ala Lys Ala Glu Lys Ser
        195                 200                 205

Lys Lys Lys Lys Glu Glu Glu Glu Asp Ser Ser Ser Glu Gly His Ala
    210                 215                 220

Asp Glu Arg Gly Thr Pro Glu Tyr Asn Ile Ser Leu Gly Glu Arg Ser
225                 230                 235                 240

Ser Ser

<210> SEQ ID NO 45
```

<211> LENGTH: 726
<212> TYPE: DNA
<213> ORGANISM: Artificial Sequence
<220> FEATURE:
<223> OTHER INFORMATION: Synthetic insert in HMGB1-CJ0113-PAL nucleotide

<400> SEQUENCE: 45

```
tcctcctcca tgggtaaagg cgacccgaaa aaaccgcgtg gtaaaatgtc ttcttacgcg    60
ttcttcgttc agacctgccg tgaagaacac aaaaaaaaac acccggacgc ttctgttaac   120
ttctctgaat tctctaaaaa atgctctgaa agatggaaaa ccatgtcttc taaagaaaaa   180
ggtaaattcg aagacatggc gaaagcggac aaactgagat acgaaaaaga atgaaaaac   240
tacgttccgc cgaaaggtga accaaaaaa aaattcaaag acccgaacgc gccgaaacgt   300
ccgccgtctg cgttcttcct gttctgcagc gaattcagac cgaaaatcaa aggtgaacac   360
ccgggtctgt ctatcggtga cgttgcgaaa aaactgggtg aaatgtggaa caacaccgcg   420
gcggacgaca acagccgta cgaaaaaaaa gcggcgaaac tgaaagaaaa atacgaaaaa   480
gacatcgcgg cgtacagagc gaaaggtaaa gttgacgcgg gtaaaaaagt tgttgcgaaa   540
gcggaaaaat ctaaaaaaaa aaaagaagaa gaagaagact cctcctccgg tgtttctatc   600
accgttgaag gtaactgcga cgaatggggt accgacgaat acaaccaggc gtcctcctcc   660
gaaggtcacg cggacgaacg tggtaccccg gaatacaaca tctctctggg tgaacgttcc   720
tcctcc                                                              726
```

<210> SEQ ID NO 46
<211> LENGTH: 182
<212> TYPE: PRT
<213> ORGANISM: Artificial Sequence
<220> FEATURE:
<223> OTHER INFORMATION: Synthetic insert in HMGB1-CJ0113-PAL amino acid

<400> SEQUENCE: 46

```
Ser Ser Ser Met Gly Lys Gly Asp Pro Lys Lys Pro Arg Gly Lys Met
  1               5                  10                  15

Ser Ser Tyr Ala Phe Phe Val Gln Thr Cys Arg Glu Glu His Lys Lys
             20                  25                  30

Lys His Pro Asp Ala Ser Val Asn Phe Ser Glu Phe Ser Lys Lys Cys
         35                  40                  45

Ser Glu Arg Trp Lys Thr Met Ser Ser Lys Glu Lys Gly Lys Phe Glu
     50                  55                  60

Asp Met Ala Lys Ala Asp Lys Leu Arg Tyr Glu Lys Glu Met Lys Asn
 65                  70                  75                  80

Tyr Val Pro Pro Lys Gly Glu Thr Lys Lys Lys Phe Lys Asp Pro Asn
                 85                  90                  95

Ala Pro Lys Arg Pro Pro Ser Ala Phe Phe Leu Phe Cys Ser Glu Phe
            100                 105                 110

Arg Pro Lys Ile Lys Gly Glu His Ala Glu Lys Ser Lys Lys Lys Lys
        115                 120                 125

Glu Glu Glu Glu Asp Ser Ser Ser Gly Val Ser Ile Thr Val Glu Gly
    130                 135                 140

Asn Cys Asp Glu Trp Gly Thr Asp Glu Tyr Asn Gln Ala Ser Ser Ser
145                 150                 155                 160
```

```
Glu Gly His Ala Asp Glu Arg Gly Thr Pro Glu Tyr Asn Ile Ser Leu
            165                 170                 175
Gly Glu Arg Ser Ser Ser
            180
```

US 10,716,840 B2

COMPOSITIONS AND METHODS OF ENHANCING IMMUNE RESPONSES TO ENTERIC PATHOGENS

CROSS-REFERENCE TO RELATED APPLICATIONS

This patent application is a continuation of U.S. 371 patent application Ser. No. 14/776,986 filed Sep. 15, 2015, and issued as U.S. Pat. No. 10,376,571 on Aug. 13, 2019, which is a national stage filing under 35 U.S.C. 371 of International Application No. PCT/US2014/027416, filed Mar. 14, 2014, which claims the benefit of priority of U.S. Provisional Patent Application No. 61/790,301, filed Mar. 15, 2013, all of which are incorporated herein by reference in their entirety.

SEQUENCE LISTING

This application is being filed electronically and includes an electronically submitted Sequence Listing in .txt format. The .txt file contains a sequence listing entitled "2014-03-14_5658-00203_ST25.txt" created on Mar. 14, 2014 and is 31,093 bytes in size. The Sequence Listing contained in this .txt file is part of the specification and is hereby incorporated by reference herein in its entirety.

INTRODUCTION

Bacterial infections still pose a significant health hazard to humans and agricultural and domesticated animals. The increase in antibiotic resistance has increased the need to move away from use of antibiotics in agriculture and the need to develop alternative methods of controlling bacterial infections and bacterial contamination of the human food supply. *Salmonella* and *E. coli* are commonly reported bacterial causes of human food-borne infections worldwide, and epidemiological evidence indicates that meat products including poultry and poultry products are a significant source of human infection. In the United States, an estimated 1.4 million cases of human Salmonellosis are reported annually. Of these cases, *S. enterica* serovars *Enteritidis* (SE) and *Typhimurium* (ST) are the most commonly isolated, although a number of other serovars have also been shown to cause enteritis in humans. Other gram negative bacteria responsible for significant infection rates include *Shigella* spp, *Vibrio* spp, *Erwinia* spp, *Klebsiella* spp, *Citrobacter* spp, *Yersinia* spp, *Providencia* spp and similar bacteria. Novel means to control these bacterial infections are needed.

SUMMARY

A vaccine vector comprising a first polynucleotide sequence encoding a PAL polypeptide is disclosed. The PAL polypeptide is a heterologous, non-natively expressed, recombinant polypeptide in the vaccine vector. The PAL polypeptide is selected from SEQ ID NO: 1, a sequence with 90% identity to SEQ ID NO: 1, such as SEQ ID NO: 6, or an immunogenic fragment thereof at least six amino acids long. The polypeptide may be expressed on the surface of the vaccine vector. The immunogenic fragment of SEQ ID NO: 1 may comprise SEQ ID NO: 2, SEQ ID NO: 3, SEQ ID NO: 4, SEQ ID NO: 5, SEQ ID NO: 36 or SEQ ID NO: 37. The vaccine vector may also comprise a second polypeptide sequence encoding an immunostimulatory polypeptide. The immunostimulatory polypeptide may also be expressed on the surface of the vaccine vector. The immunostimulatory polypeptide may be a CD154 polypeptide capable of binding CD40 or an HMGB1 polypeptide. The CD154 polypeptides include fewer than 50 amino acids and comprise amino acids 140-149, or a homolog thereof.

Vaccines according to the present invention may be comprised within a vector, such as a virus, yeast, bacterium, or liposome. In one aspect, the vaccines include polynucleotides encoding polypeptides of SEQ ID NO: 42, 44 or 46 or a sequence having 90% identity to one of these sequences. Pharmaceutical compositions may be comprised of the vaccine vectors described herein and a pharmaceutically acceptable carrier.

In still another aspect, methods of enhancing the immune response against a gram-negative bacterium in a subject by administering a vaccine vector described herein to the subject are provided. The enhanced immune response may be an enhanced antibody response, an enhanced T cell response or a combination thereof.

In a still further aspect, methods of reducing morbidity or mortality associated with infection with a gram-negative bacterium in a subject by administering a vaccine vector as described herein to the subject are provided. The vaccine vector is capable of reducing the morbidity and mortality associated with subsequent infection with a gram-negative bacterium in subjects administered the vaccine vector as compared to controls.

BRIEF DESCRIPTION OF THE DRAWINGS

FIG. 1 is a graph showing the PAL sequence-specific serum IgG antibody levels as determined by ELISA with synthetic PAL-BSA as the coating antigen on day 17 post vaccination by oral gavage with either saline, or *Bacillus* backbone (BS BB) or PAL-vectored BS vaccine (BS PAL) candidates at $10^8$ cfu/chick. The results are presented as mean S/P ratios±SEM (n=10). Groups with different upper case letters are significantly different using an ANOVA (P<0.05).

FIG. 2 is a graph showing the PAL sequence-specific ileal sIgA antibody levels as determined by ELISA with synthetic PAL-BSA as the coating antigen on day 17-post vaccination by oral gavage with either saline, or *Bacillus* backbone (BS BB) or PAL-vectored BS vaccine candidates (BSNNP) at $10^8$ cfu/chick. The results are presented as mean S/P ratios±SEM (n=10). Groups with different upper case letters are significantly different using an ANOVA (P<0.05).

DETAILED DESCRIPTION

Figure 3:
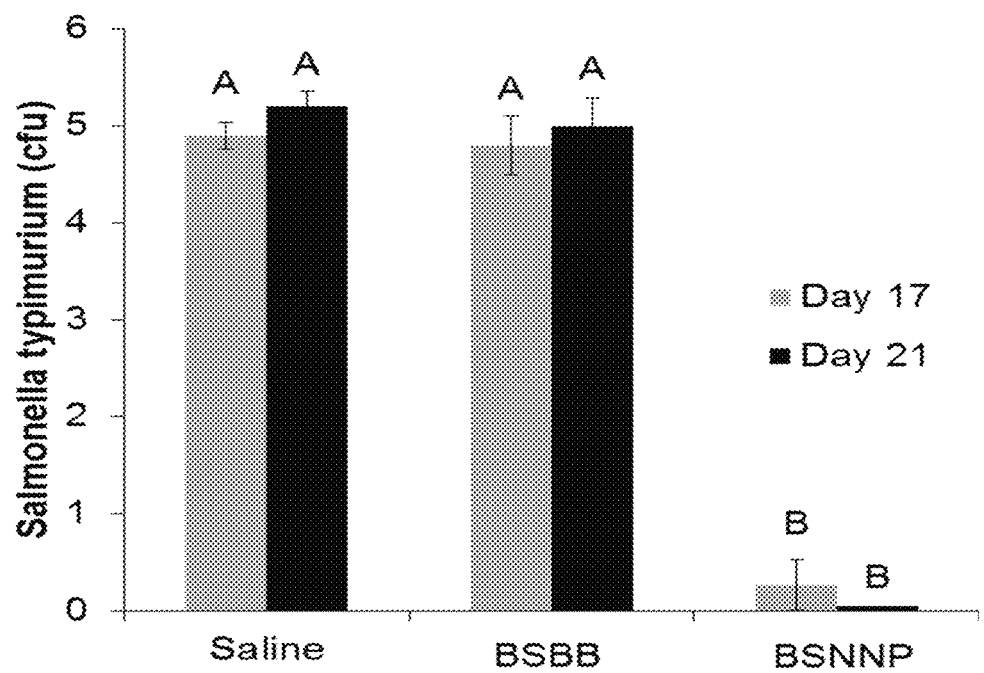
FIG. 3 is a graph in which *Salmonella typhimurium* was enumerated in chicks receiving saline, BSBB or PAL-BS construct vectored vaccine (BSNNP) at $10^8$ cfu/chick using conventional microbiological plate counting at 17 and 21 days post hatch. All groups received ST challenge dose of $1\times10^8$ cfu/ml on day 11 post-hatch. The results are presented as mean $\log_{10}$ cfu/gram of cecal content+SEM (n=10). Groups with different upper case letters are significantly different by ANOVA (P<0.05).

Conventional vaccines against gram-negative bacteria are generally based on live/attenuated bacteria that are delivered in controlled numbers often via injection. Gram-negative bacteria are quite diverse and antigenic diversity among the different species of bacteria and even among different strains within the same species has made vaccination against more than a single strain or serovar difficult. Recombinant vaccines have been developed but because of the antigenic diversity are generally restricted to enhancing an immune response to a single species or even a single strain of bacteria. A vaccine capable of protecting against multiple serovars and indeed against more than one species of gram-negative bacteria would be optimal. In addition, a vaccine that could be given orally would make administration cheaper and compliance more likely. A vaccine comprising a highly conserved region of PAL, a peptidoglycan-associated lipoprotein found broadly on gram-negative organisms, is provided.

Recombinant DNA technologies enable relatively easy manipulation of many yeast, bacterial and viral species. Some microorganisms are mildly pathogenic or non-pathogenic, but are capable of generating a robust immune response. These microorganisms make attractive vaccine vectors for eliciting an immune response to antigens recombinantly expressed in the vector. Vaccines vectored by microorganisms may mimic a natural infection, help produce robust and long lasting mucosal immunity, and may be relatively inexpensive to produce and administer. Many of these vaccine vectors can be administered orally which reduces the cost and need for professionals for administration and lowers resistance to administration. In addition, such vectors can often carry more than one antigen and have potential to provide protection against multiple infectious agents.

A vaccine includes any composition comprising a polynucleotide encoding an antigenic polypeptide that is capable of eliciting an immune response to the polypeptide. A vaccine vector is a composition that can be engineered to carry antigens and optionally other immunostimulatory polypeptides and may also comprise an adjuvant or be administered with an adjuvant to further increase the immune response to the parasite and provide better protection from morbidity and mortality associated with a subsequent infection. The use of vectors, such as bacterial, viral or yeast vectors, for vaccination and generation of immune responses against enteric pathogens is disclosed herein. The enteric pathogens may include, but are not limited to *E. coli*, *Salmonella* and the other enteric microorganisms disclosed in Table 1 in the Examples. The immune responses after administration of the vaccine vectors described herein need not be fully protective, but may decrease the morbidity or percentage mortality (i.e. likelihood of mortality) associated with subsequent infection with an enteric pathogen.

In one aspect, a vaccine vector comprising a first polynucleotide sequence encoding at least one of SEQ ID NO: 1-6, 32, 36 or 37 or an immunogenic fragment at least six amino acids long of any one of these sequences is provided. The vaccine vector may also include a second polynucleotide encoding an immunostimulatory polypeptide is provided. Suitably the PAL polypeptide or immunogenic fragments thereof and the immunostimulatory polypeptide are expressed on the surface of the vaccine vector. The immunogenic fragments of the polypeptide of SEQ ID NO: 1 may comprise any one of or a combination of SEQ ID NOs: 2-5 or 36-40 or any other fragment of at least six amino acids. For example, the antigenic polypeptide may comprise, may consist essentially of or may consist of SEQ ID NO: 1, SEQ ID NO: 2, SEQ ID NO: 3, SEQ ID NO: 4, SEQ ID NO: 5, SEQ ID NO: 6, SEQ ID NO: 32, SEQ ID NO: 36, SEQ ID NO: 37 or an immunogenic fragment or combination of any of these SEQ ID NOs.

An immunogenic fragment of the antigenic polypeptide may be a sequence that is at least 6, 8, 10, 12, 14, 16, 18 or 20 amino acids long and has at least 85%, 90%, 92%, 94%, 95%, 96%, 97%, 98% or 99% percent identity to the SEQ ID NOs provided herein. A vaccine includes any composition comprising a polynucleotide encoding an antigenic polypeptide that is capable of eliciting an immune response to the polypeptide in a subject administered the vaccine. The use of vectors, such as bacterial vectors, for vaccination and generation of immune responses against enteric bacteria, including but not limited to *Salmonella* spp, *Escherichia* spp, *Shigella* spp, *Vibrio* spp, *Erwinia* spp, *Klebsiella* spp, *Citrobacter* spp, *Yersinia* spp, *Providencia* spp or similar bacteria such as those listed in Table 1 is disclosed.

Polynucleotides encoding the antigenic polypeptides provided herein and other antigens from any number of pathogenic organisms may be inserted into the vector and expressed in the vector. The expression of these polynucleotides by the vector will allow generation of an immune response to the antigenic polypeptides following immunization of the subject. The polynucleotides may be inserted into the chromosome of the vector or encoded on plasmids or other extrachromosomal DNA. Those of skill in the art will appreciate that numerous methodologies exist for obtaining expression of polynucleotides in vectors such as *Salmonella* or *Bacillus*. The polynucleotides may be operably connected to a promoter (e.g., a constitutive promoter, an inducible promoter, etc.) by methods known to those of skill in the art. Suitably, polynucleotides encoding antigenic polypeptides are inserted into a vector, e.g., a bacterial vector, such that the polynucleotide is expressed.

The polynucleotides encoding PAL or other antigenic polypeptides may be inserted in frame in a polynucleotide encoding a transmembrane protein. The polynucleotide encoding the antigenic polypeptide may be inserted into the vector polynucleotide sequence to allow expression of the antigenic polypeptide on the surface of the vector. For example, the polynucleotide encoding antigenic polypeptide may be inserted in frame into the vector polynucleotide in a region encoding an external loop region of a transmembrane protein such that the vector polynucleotide sequence remains in frame. In one embodiment, the first polynucleotide encoding the antigenic polypeptide may be inserted into loop 9 of the lamB gene of *Salmonella* as described in the Examples. Alternatively, the polynucleotide could be inserted in a polynucleotide such as the cotB gene of *Bacillus*.

In another embodiment, the first polynucleotide is inserted into or at a surface exposed end of a protein that is attached to the cell wall, but is not a transmembrane protein. The protein may be a secreted protein that is anchored or attached to the cell wall via a protein or lipid anchor. For examples, the polynucleotide may be inserted at the 3' end of the fibronectin binding protein (FbpB) of *Bacillus subtilis*. Alternatively, the first polynucleotide encoding the antigenic polypeptide may be inserted into a polynucleotide encoding a secreted polypeptide.

Those of skill in the art will appreciate that the polynucleotide encoding the antigenic polypeptide could be inserted in a wide variety of vector polynucleotides to provide expression and presentation of the antigenic polypeptide to the immune cells of a subject treated with the vaccine. The polynucleotide encoding the antigenic polypeptide may be included in a single copy or more than one copy. The multiple copies may be inserted in a single location or more than one location within the vaccine vector chromosome or extrachromosomally.

Suitably the first polynucleotide encodes SEQ ID NO: 1, SEQ ID NO: 6 or an immunogenic fragment thereof at least six or more amino acids such as SEQ ID NO: 2-5, or 36-40. The vector may include more than one copy of the first polynucleotide or may include multiple antigenic polynucleotides targeted to the same or different pathogens. In the Examples, SEQ ID NOs: 1-6, 32, 36 and 37 were shown to be immunogenic. SEQ ID NOs: 1 (EGHADERGTPEYNISLGER) and 8 (TVEGHADERGTPEYNISLG) are incorporated into a *Bacillus* or *Salmonella* vector in the Examples. The combination of epitopes from more than one polypeptide from a single pathogen or target or the combination of epitopes from distinct pathogens or targets is specifically contemplated. The polynucleotides may be inserted into the vector separately or may be inserted as a fusion protein containing more than a single epitope. In the Examples, SEQ ID NOs: 1 (PAL) and 31 (CJ0113) were incorporated into a *Bacillus* vector (see SEQ ID NO: 42, 44 and 46 and the Examples). Suitably, the portion of the antigenic polypeptide inserted into the vector is immunogenic. An immunogenic fragment is a peptide or polypeptide capable of eliciting a cellular or humoral immune response or capable of reducing morbidity or mortality associated with subsequent infection with the target pathogen or a related pathogen.

An antigenic polypeptide includes any polypeptide that is immunogenic. The antigenic polypeptides include, but are not limited to, antigens that are pathogen-related, allergen-related, tumor-related or disease-related. Pathogens include viral, parasitic, fungal and bacterial pathogens as well as protein pathogens such as the prions. The antigenic polypeptides may be full-length proteins or portions thereof. It is well established that immune system recognition of many proteins is based on a relatively small number of amino acids, often referred to as the epitope. Epitopes may be only 4-8 amino acids. Thus, the antigenic polypeptides described herein may be full-length sequences, four amino acid long epitopes or any portion between these extremes. In fact the antigenic polypeptide may include more than one epitope from a single pathogen or protein. The antigenic polypeptides may have at least 85%, 90%, 92%, 94%, 95%, 96%, 97%, 98% or 99% percent identity to the SEQ ID NOs provided herein. Suitably, an antigenic fragment of a polypeptide may be four, five, six, seven, eight, nine, ten, twelve, fifteen, seventeen or more consecutive amino acids, of SEQ ID NO: 1-6, 32, 36 or 37.

Multiple copies of the same epitope or multiple epitopes from different proteins may be included in the vaccine vector. The epitopes in the vaccine vector may be related and homologous to allow targeting of multiple related pathogens with a single vaccine vector. It is envisioned that several epitopes or antigens from the same or different pathogens or diseases may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time, providing broader protection against multiple strains of a single pathogen or a more robust immune response against a single pathogen. In the Examples, the vaccine vectors included the PAL antigenic polypeptide of SEQ ID NO: 1 and a *Campylobacter* antigenic polypeptide of SEQ ID NO: 31 already demonstrated to be effective to enhance the immune response to *Campylobacter* in International Patent Publication No. WO2011/156619.

Those of skill in the art will appreciate that the antigenic polypeptides from other pathogens may be used in the vaccine vectors to enhance the immune response against more than one pathogen by a single vaccine. It would be advantageous to administer a single vaccine directed against multiple pathogens. A vaccine capable of eliciting an immune response to an enteric pathogen, such as *E. coli*, in combination with Influenza, *Salmonella, Campylobacter* or other pathogens is envisioned. For example, the second antigenic polypeptide may be an Influenza polypeptide, suitably it is an Influenza H5N1 polypeptide or a polypeptide associated with multiple strains of the Influenza virus such as a polypeptide of the Influenza M2 protein. The ectodomain of the Influenza A virus M2 protein, known as M2e, protrudes from the surface of the virus. The M2e portion of the M2 protein contains about 24 amino acids. The M2e polypeptide varies little from one isolate to the next within Influenza. In fact, only a few naturally occurring mutations in M2e have been isolated from infected humans since the 1918 flu epidemic. In addition, influenza viruses isolated from avian and swine hosts have different, yet still conserved, M2e sequences. For reviews of the M2e polypeptide sequences isolated from human, avian and swine hosts see Liu et al., Microbes and Infection 7:171-177 (2005) and Reid et al., J. Virol. 76:10717-10723 (2002) each of which are incorporated herein by reference in its entirety. Suitably the entire M2e polypeptide may be inserted into the vaccine vector or only a portion may be used. An eight amino acid polypeptide (LM2 having amino acid sequence: EVETPIRN, SEQ ID NO: 9 or its variant M2eA having amino acid sequence EVETPTRN, SEQ ID NO: 10) was incorporated into the vaccine vector and demonstrated to produce an antibody response after administration to chickens. See U.S. Publication No. 2011/0027309 which is incorporated herein by reference in its entirety.

Other suitable epitopes for inclusion in a vaccine vector to enhance an immune response to Influenza A include, but are not limited to, polypeptides of the hemagglutinin (HA) or the nuclear protein (NP) of Influenza A. For example, the peptides of SEQ ID NO: 11, SEQ ID NO: 12, SEQ ID NO: 13, or SEQ ID NO: 14 may be included in a vaccine vector.

One of skill in the art will appreciate that any of these sequences may be used in combination with any other epitope including epitopes derived from other pathogens or antigens.

For example, the PAL antigenic polypeptide provided herein may be combined with other antigenic polypeptides from gram negative bacteria such as those provided in U.S. Patent Publication No. US2011/0159026 or International Publication No. WO 2011/156619, both of which are incorporated by reference herein in their entireties. The combination of multiple antigenic polypeptides, one of which provides broad immunity to multiple gram negative bacteria and others that are more specific to particular gram negative bacteria may provide superior protection from subsequent infection.

Immunostimulatory molecules included as part of the vaccine vector could potentially activate parts of the immune system critical to long-lasting protection. Immunostimulatory polypeptides may be polypeptides capable of stimulating a naïve or adaptive immune response. The immunostimulatory polypeptides are not natively associated with the vaccine vector and are polypeptides natively associated with a vertebrate immune system, such as that of the subject to which the vaccine will be administered. Two immunostimulatory polypeptides are described herein, namely CD154 and High Mobility Group Box 1 (HMGB1) polypeptides, but one of skill in the art will appreciate that other immunostimulatory polypeptides could be used or alternatively could be used in combination with those described herein.

Additional polynucleotides encoding polypeptides involved in triggering the immune system may also be included in a vaccine vector. The polynucleotides may encode immune system molecules known for their stimulatory effects, such as an interleukin, Tumor Necrosis Factor, interferon, or another polynucleotide involved in immune-regulation. The vaccine may also include polynucleotides encoding peptides known to stimulate an immune response, such as the CD154 or HMGB1 polypeptides described herein.

HMGB1 is secreted by activated macrophages and damaged cells, and acts as a cytokine mediator of inflammation, affecting the innate immune response. Portions of the HMGB1 sequence have been included in the vaccine vectors described in the Examples. The HMGB1 (High Mobility Group Box-1) protein was first identified as a DNA-binding protein critical for DNA structure and stability. It is a ubiquitously expressed nuclear protein that binds DNA with no sequence specificity. The protein is highly conserved and found in plants to mammals. The zebrafish, chicken and human HMGB1 amino acid sequences are provided in SEQ ID NO: 23, SEQ ID NO: 15 and SEQ ID NO: 22, respectively. The sequence throughout mammals is highly conserved with 98% amino acid identity and the amino acid changes are conservative. Thus an HMGB1 protein from one species can likely substitute for that from another species functionally. The full-length HMGB1 protein or a portion thereof may be used as the HMGB1 polypeptide in the vaccine vectors described herein. HMGB1 has two DNA binding regions termed A box as shown in SEQ ID NO: 16 and 17 and B box as shown in SEQ ID NO: 18 and 19. See Andersson and Tracey, Annu. Rev. Immunol. 2011, 29:139-162, which is incorporated by reference herein in its entirety.

HMGB1 is a mediator of inflammation and serves as a signal of nuclear damage, such as from necrotic cells. HMGB1 can also be actively secreted by cells of the monocyte/macrophage lineage in a process requiring acetylation of the protein, translocation across the nucleus and secretion. Extracellular HMGB1 acts as a potent mediator of inflammation by signaling via the Receptor for Advanced Glycated End-products (RAGE) and via members of the Toll-like Receptor family (TLR), in particular TLR4. The RAGE binding activity has been identified and requires the polypeptide of SEQ ID NO: 20. TLR4 binding requires the cysteine at position 106 of SEQ ID NO: 15, which is found in the B box region of HMGB1.

The inflammatory activities of HMGB1 do not require the full-length protein and functional fragments have been identified. The B box has been shown to be sufficient to mediate the pro-inflammatory effects of HMGB1 and thus SEQ ID NO: 18 and 19 are HMGB1 polypeptides or functional fragments thereof within the context of the present invention. In addition, the RAGE binding site and the pro-inflammatory cytokine activity have been mapped to SEQ ID NO: 20 and SEQ ID NO: 21, respectively. Thus, these polypeptides are functional fragments of HMGB1 polypeptides in the context of the present invention.

Those of skill in the art are capable of identifying HMGB1 polypeptides and fragments thereof capable of stimulating pro-inflammatory cytokine activity, using methods such as those in International Publication No. WO02 092004, which is incorporated herein by reference in its entirety. Suitably, the HMGB1 polypeptide includes the RAGE binding domain at amino acids 150-183 of SEQ ID NO:15 (SEQ ID NO: 20 or a homolog thereof) and the pro-inflammatory cytokine activity domain between amino acids 89-109 of SEQ ID NO: 15 (SEQ ID NO: 21 or a homolog thereof). In particular, HMGB1 polypeptides and functional fragments or homologs thereof include polypeptides identical to, or at least 99% identical, at least 98% identical, at least 95% identical, at least 90% identical, at least 85% identical, or at least 80% identical to the HMGB1 polypeptides of SEQ ID NOs: 15 or 16-23.

As described in more detail below, a vaccine vector may include a CD154 polypeptide that is capable of binding CD40 in the subject and stimulating the subject to respond to the vector and its associated antigen. Involvement of dendritic cells (DCs) is essential for the initiation of a powerful immune response as they possess the unique ability to activate naïve T cells, causing T cell expansion and differentiation into effector cells. It is the role of the DC, which is an antigen presenting cell (APC) found in virtually all tissues of the body, to capture antigens, transport them to associated lymphoid tissue, and then present them to naïve T cells. Upon activation by DCs, T cells expand, differentiate into effector cells, leave the secondary immune organs, and enter peripheral tissues. Activated cytotoxic T cells (CTLs) are able to destroy virus-infected cells, tumor cells or even APCs infected with intracellular parasites (e.g., *Salmonella*) and have been shown to be critical in the protection against viral infection. CD40 is a member of the TNF-receptor family of molecules and is expressed on a variety of cell types, including professional antigen-presenting cells (APCs), such as DCs and B cells. Interaction of CD40 with its ligand CD154 is extremely important and stimulatory for both humoral and cellular immunity. Stimulation of DCs via CD40, expressed on the surface of DCs, can be simulated by anti-CD40 antibodies. In the body, however, this occurs by interaction with the natural ligand for CD40 (i.e. CD154) expressed on the surface of activated T-cells. Interestingly, the CD40-binding regions of CD154 have been identified. The CD40-binding region of CD154 may be expressed on the surface of a vector, such as a *Salmonella* or *Bacillus* vector, and results in an enhanced immune response against a co-presented peptide sequence as shown in the Examples provided herein and in U.S. Patent Publication No. 2011/0027309, which is incorporated herein by reference in its entirety. A CD154 polypeptide may be a portion of CD154 full-length protein or the entire CD154 protein. Suitably, the CD154 polypeptide is capable of binding CD40.

As discussed above, a CD154 polynucleotide encoding a CD154 polypeptide that is capable of enhancing the immune response to the antigen may be included in the vaccine. Suitably, the CD154 polypeptide is fewer than 50 amino acids long, more suitably fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among the various species. The CD154 sequences of chicken and human are provided in SEQ ID NO: 24 and SEQ ID NO: 25, respectively.

The CD40 binding regions of CD154 have been determined for a number of species, including human, chicken, duck, mouse and cattle and are shown in SEQ ID NO: 26, SEQ ID NO: 27, SEQ ID NO: 28, SEQ ID NO: 29, and SEQ ID NO: 30, respectively. Although there is variability in the sequences in the CD40 binding region between species, the human CD154 polypeptide was able to enhance the immune response in chickens. Therefore, one may practice the invention using species specific CD154 polypeptides or a heterologous CD154 polypeptide. Thus the CD154 polypeptides of SEQ ID NO: 24-30 may be included in a vaccine vector or a polypeptide at least 99, 98, 97, 96, 95, 93, 90 or 85% identical to the sequences of SEQ ID NO: 24-30 may be included in a vaccine vector.

The polypeptide from CD154 stimulates an immune response at least in part by binding to its receptor, CD40. A polypeptide homologous to the CD154 polypeptide which is expressed on immune cells of the subject and which is capable of binding to the CD40 receptor on macrophages and other antigen presenting cells. Binding of this ligand-receptor complex stimulates macrophage (and macrophage lineage cells such as dendritic cells) to enhance phagocytosis and antigen presentation while increasing cytokine secretions known to activate other local immune cells (such as B-lymphocytes). As such, molecules associated with the CD154 peptide are preferentially targeted for immune response and expanded antibody production.

The antigenic polypeptides and the immunostimulatory polypeptides are delivered via a vaccine vector. The vaccine vectors may be bacterial, yeast, viral or liposome-based vectors. Potential vaccine vectors include, but are not limited to, Bacillus (Bacillus subtilis), Salmonella (Salmonella enteritidis), Shigella, Escherichia (E. coli), Yersinia, Bordetella, Lactococcus, Lactobacillus, Streptococcus, Vibrio (Vibrio cholerae), Listeria, yeast such as Saccharomyces, or Pichia, adenovirus, poxvirus, herpesvirus, alphavirus, and adeno-associated virus. Live bacterial, yeast or viral vaccine vectors may still pose risks to immunocompromised individuals and require additional regulatory scrutiny. Thus use of vectors that are killed or inactivated or qualify as Generally Recognized As Safe (GRAS) organisms by the Food and Drug Administration (FDA) is desirable. The problem is generating a robust immune response using such vectors. Methods of inactivating or killing bacterial, yeast or viral vaccine vectors are known to those of skill in the art and include, but are not limited to methods such as formalin inactivation, antibiotic-based inactivation, heat treatment and ethanol treatment. By including an immunostimulatory polypeptide such as HMGB1 (high mobility group box 1) polypeptide on the surface of the vaccine vector we can generate a robust immune response against an antigenic polypeptide using a Bacillus spp. vector or other GRAS vector. In fact, such vectors can be inactivated such that it cannot replicate and still elicit a robust immune response after administration. The vaccine vectors may be wild-type bacteria, yeasts or viruses that are not pathogenic. Alternatively the vectors may be attenuated such that the vector has limited ability to replicate in the host or is not capable of growing without supplemented media for more than a few generations. Those of skill in the art will appreciate that there are a variety of ways to attenuate vectors and means of doing so.

At least a portion of the antigenic polypeptide and at least a portion of the immunostimulatory polypeptide are present or expressed on the surface of the vaccine vector. Present on the surface of the vaccine vector includes polypeptides that are comprised within an external loop of a transmembrane protein, interacting with, e.g., covalently or chemically cross-linked to, a transmembrane protein, a membrane lipid or membrane anchored carbohydrate or polypeptide. A polypeptide can be comprised within a transmembrane protein by having the amino acids comprising the polypeptide linked via a peptide bond to the N-terminus, C-terminus or anywhere within the transmembrane protein (i.e. inserted between two amino acids of the transmembrane protein or in place of one or more amino acids of the transmembrane protein (i.e. deletion-insertion)). Suitably, the polypeptides may be inserted into an external loop of a transmembrane protein. Suitable transmembrane proteins are srtA, cotB and lamB, but those of skill in the art will appreciate many suitable transmembrane proteins are available. Polypeptides may be linked to a membrane or cell wall anchored protein or lipid such that the antigenic polypeptide and the immunostimulatory polypeptide are expressed on the surface of the vaccine vector.

As described above, polynucleotides encoding the antigenic or immunostimulatory polypeptides may be inserted into the chromosome of the vector or maintained extrachromosomally (e.g., on a plasmid, BAC or YAC). One of skill in the art will appreciate that these polynucleotides can be inserted in frame in a variety of polynucleotides and expressed in different parts of the vector or may be secreted. The polynucleotide encoding the immunostimulatory polypeptide capable of enhancing the immune response to the antigenic polypeptide may also encode the antigenic polypeptide. The polynucleotide encoding the antigenic polypeptide may be linked to the polynucleotide encoding the immunostimulatory polypeptide, such that in the vector, the two polypeptides are portions of the same polypeptide. In the Examples, a polynucleotide encoding the antigenic polypeptide also encodes the immunostimulatory polypeptide. In one embodiment, the two polynucleotides encoding the polypeptides are both inserted in frame in loop 9 of the lamB gene of Salmonella enteritidis or another vaccine vector. Those of skill in the art will appreciate that bacterial polynucleotides encoding other transmembrane proteins and other loops of the lamB gene may also be used.

Alternatively, the polynucleotide encoding the antigenic polypeptide and/or the immunostimulatory polypeptide may be inserted into a secreted polypeptide that is displayed or presented on the surface of the vaccine vector through association with a protein, lipid or carbohydrate on the surface of the vaccine vector. Those of skill in the art will appreciate that the polynucleotide encoding the antigenic polypeptide and/or the immunostimulatory polypeptide could be inserted in a wide variety of vaccine vector polynucleotides to provide expression and presentation of the antigenic polypeptide and/or the immunostimulatory polypeptide to the immune cells of a subject treated with the vaccine vector. The coding region of the PAL antigenic polypeptide and the immunostimulatory polypeptide can be fused to the C-terminus of the *Staphylococcus aureus* fibronectin binding protein containing a sorting motif for sortase from *Listeria*. This allows the secreted proteins to be anchored on the cell wall of gram positive bacteria such as *Bacillus*. See Nguyen and Schumann, J Biotechnol (2006) 122: 473-482, which is incorporated herein by reference in its entirety. Other similar methods may also be used.

Alternatively, the polypeptides may be covalently or chemically linked to proteins, lipids or carbohydrates in the membrane, cell wall, or capsid if a viral vector is being used through methods available to persons of skill in the art. For example, di-sulfide bonds or biotin-avidin cross-linking could be used to present the antigenic and immunostimulatory polypeptides on the surface of a vaccine vector. Suitably, the antigenic polypeptide and the immunostimulatory polypeptide are part of a fusion protein. The two polypeptides may be directly linked via a peptide bond or may be separated by a linker, spacer, or a section of a third protein into which they are inserted. In the Examples, an amino acid spacer was used between the polypeptides. A spacer may be between 2 and 20 amino acids, suitably between 3 and 10 amino acids, suitably between 6 and 8 amino acids. Suitably the amino acids in the spacer have a small side chain and are not charged, such as glycine, alanine or serine. Spacers may have combinations of amino acid residues.

In the Examples, the vaccine vectors have the antigenic polypeptides (SEQ ID NO: 1 and SEQ ID NO: 31 (Campy CJ0113)) and the immunostimulatory polypeptide (HMGB1) encoded on the same polynucleotide and in frame with each other. See SEQ ID NO: 42, 44, and 46. Notably, in the Examples using a three amino acid spacer between each of the polypeptide fragments, the vaccine vector in which HMGB1 polypeptide was positioned on either the N- or C-terminal end of the vaccine vector insert resulted in the best protection against subsequent infection. The best performing vaccine vector had CJ0113 followed by PAL followed by HMGB1 (from N- to C-terminal or SEQ ID NO: 42). Thus the order or display of the antigens and immunostimulatory polypeptides on the surface of the vaccine vector may affect the immune response. In alternative embodiments, the immunostimulatory polypeptide and the antigenic polypeptide may be encoded by distinct polynucleotides. Those of skill in the art will appreciate that a variety of methods may be used to obtain expression of the antigenic polypeptide and the HMGB1 polypeptide on the surface of the vaccine vector. Such methods are known to those skilled in the art.

Compositions comprising the vaccine vector and a pharmaceutically acceptable carrier are also provided. A pharmaceutically acceptable carrier is any carrier suitable for in vivo administration. Suitably, the pharmaceutically acceptable carrier is acceptable for oral, nasal or mucosal delivery. The pharmaceutically acceptable carrier may include water, buffered solutions, glucose solutions or bacterial culture fluids. Additional components of the compositions may suitably include excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The vaccine vector in the compositions may not be capable of replication, suitably the vaccine vector is inactivated or killed prior to addition to the composition.

Methods of enhancing immune responses in a subject by administering a vaccine vector are also provided. The vaccine vector may contain a first polynucleotide encoding an antigenic PAL polypeptide of SEQ ID NO: 1-6, 32, 36, 37 or an immunogenic fragment thereof. The vaccine vector may also include a second polynucleotide encoding an immunostimulatory polypeptide. The immunostimulatory polypeptide is suitably a polypeptide natively associated with a vertebrate immune system and involved in stimulating an immune response. The immunostimulatory polypeptide may stimulate the native or adaptive immune response of the subject. Suitably a HMGB1 polypeptide or a CD154 polypeptide as described more fully above may be used as the immunostimulatory polypeptide. In the methods provided herein, the vaccine vector comprising an antigenic PAL polypeptide and optionally an immunostimulatory polypeptide is administered to a subject in an amount effective to enhance the/effect an immune response of the subject to the vaccine vector and in particular to the antigenic polypeptide and suitably to gram-negative bacteria such as *Salmonella* and *E. coli*.

The enhanced immune response may include an antibody or T cell response. Suitably the immune response is a protective immune response, but the immune response may not be fully protective, but may be capable of reducing the morbidity or mortality associated with infection. The immunostimulatory polypeptides may be used to enhance the immune response in the subject to any foreign antigen or antigenic polypeptide present in the vaccine vector in addition to the antigenic PAL polypeptide. One of skill in the art will appreciate that the immunostimulatory polypeptide could be used to enhance the immune response to more than one antigenic polypeptide present in a vaccine vector. Enhancing an immune response includes, but is not limited to, inducing a therapeutic or prophylactic effect that is mediated by the immune system of the subject. Specifically, enhancing an immune response may include, but is not limited to, enhanced production of antibodies, enhanced class switching of antibody heavy chains, maturation of antigen presenting cells, stimulation of helper T cells, stimulation of cytolytic T cells or induction of T and B cell memory.

Suitably, the vaccine vector contains a polynucleotide encoding a polypeptide including amino acids 150-183 and 89-109 of the HMGB1 polypeptide (SEQ ID NO: 15) or a homolog thereof. In the Examples, a 190 amino acid polypeptide of HMGB1 was used. Suitably, the polynucleotide encodes a HMGB1 polypeptide from the same species as the subject. Heterologous combinations of HMGB1 polypeptides and subjects (e.g. a human HMGB1 polypeptide for use in a chicken vaccine) may be useful in the methods of the invention because HMGB1 is highly conserved through a wide number of species. The HMGB1 polypeptide may be used to enhance the immune response in the subject to any foreign antigen, antigenic polypeptide or more than one polypeptide present in or on the vaccine vector. One of skill in the art will appreciate that the HMGB1 polypeptide could be used to enhance the immune response to more than one antigenic polypeptide present in a vaccine vector. The polypeptide from HMGB1 stimulates an immune response at least in part by activating dendritic cells and macrophages and thus stimulating production of cytokines such as IL-1, IL-6, IFN-γ and TNF-α. In the Examples, a polypeptide of HMGB1 was expressed on the surface of the vaccine vector.

The vaccine vector may suitably contain a CD154 polypeptide capable of binding to CD40 and activating CD40. The vaccine comprising the polynucleotide encoding a CD154 polypeptide capable of binding to CD40 is administered to a subject in an amount effective to enhance or effect the immune response of the subject to the vaccine. Suitably, the vaccine contains a polynucleotide encoding a polypeptide including amino acids 140-149 of the human CD154 polypeptide (SEQ ID NO: 25) or a homolog thereof. As noted above, a homologue of amino acid 140-149 derived from one species may be used to stimulate an immune response in a distinct species. Suitably, the polynucleotide encodes a CD154 polypeptide from the same species as the subject. Suitably, a polynucleotide encoding the polypeptide of SEQ ID NO: 26 is used in human subjects, a polynucleotide encoding the polypeptide of SEQ ID NO: 27 is used in chickens, a polynucleotide encoding the polypeptide of SEQ ID NO: 28 is used in ducks, a polynucleotide encoding the polypeptide of SEQ ID NO: 29 is used in mice, and a polynucleotide encoding the polypeptide of SEQ ID NO: 30 is used in cows. The human CD154 polypeptide (SEQ ID NO: 26) has been used in a chicken vaccine and was demonstrated to enhance the immune response to a foreign antigen. Thus other heterologous combinations of CD154 polypeptides and subjects may be useful in the methods of the invention.

In addition, methods of enhancing an immune response against a gram negative bacterium selected from *Salmonella* spp, *Escherichia* spp, *Shigella* spp, *Vibrio* spp, *Erwinia* spp, *Klebsiella* spp, *Citrobacter* spp, *Yersinia* spp, *Providencia* spp and similar bacteria and methods of reducing morbidity associated with subsequent infection with a gram-negative bacterium are disclosed. Briefly, the methods comprise administering to a subject a vaccine vector comprising a first polynucleotide sequence encoding an antigenic PAL polypeptide and optionally a second polynucleotide encoding an immunostimulatory polypeptide in an effective amount. The antigenic PAL polypeptides may include SEQ ID NO: 1-6. The insertion of the antigenic PAL polypeptides into the vector may be accomplished in a variety of ways known to those of skill in the art, including but not limited to the scarless site-directed mutation system described in BMC Biotechnol. 2007 September, 17: 7(1): 59, Scarless and Site-directed Mutagenesis in *Salmonella Enteritidis* chromosome, which is incorporated herein by reference in its entirety and the method used herein as described in Nguyen and Schumann J Biotechnol 2006 122: 473-482, which is incorporated herein by reference in its entirety. The vector may also be engineered to express the antigenic PAL polypeptides in conjunction with other antigenic polypeptides from other pathogens including viruses such as Influenza M2e or bacteria such as *Salmonella, Campylobacter* or *E. coli*. In particular, a polypeptide of CD154 capable of binding CD40 or HMGB1 may be expressed by the vector to enhance the immune response of the subject to the antigenic PAL polypeptide.

The compositions containing antigenic polypeptides may also be used to decrease the morbidity associated with subsequent infection by a gram-negative bacterium. The compositions may prevent the bacterium from causing disease or may limit or reduce any associated morbidity in a subject to which the compositions or vaccine vectors described herein were administered. The compositions and vaccine vectors described herein may reduce the severity of subsequent disease by decreasing the length of disease, weight loss, severity of symptoms of the disease, decreasing the morbidity or mortality associated with the disease or reducing the likelihood of contracting the disease. The compositions may also reduce the spread of the pathogen by inhibiting transmission. The morbidity or mortality associated with the disease after administration of the vaccine vectors described herein may be reduced by 25%, 30%, 40%, 50%, 60%, 70%, 80%, 90% or even 100% as compared to similar subjects not provided the vaccine vector.

For administration to animals or humans, the compositions may be administered by a variety of means including, but not limited to, intranasally, mucosally, by spraying, intradermally, parenterally, subcutaneously, intraperitonelly, intravenously, intracrannially, orally, by aerosol or intramuscularly. Eye-drop administration, oral gavage or addition to drinking water or food is additionally suitable. For poultry, the compositions may be administered in ovo.

Some embodiments of the invention provide methods of enhancing immune responses in a subject. Suitable subjects may include, but are not limited to, vertebrates, suitably mammals, suitably a human, and birds, suitably poultry such as chickens or turkeys. Other animals such as cows, cats, dogs or pigs may also be used. Suitably, the subject is non-human and may be an agricultural animal.

The useful dosage of the vaccine to be administered will vary depending on the age, weight and species of the subject, the mode and route of administration and the type of pathogen against which an immune response is sought. The composition may be administered in any dose sufficient to evoke an immune response. It is envisioned that doses ranging from $10^3$ to $10^{10}$ vector copies (i.e. colony forming units or plaque forming units), from $10^4$ to $10^9$ vector copies, or from $10^5$ to $10^7$ vector copies are suitable.

The composition may be administered only once or may be administered two or more times to increase the immune response. For example, the composition may be administered two or more times separated by one week, two weeks, three weeks, 1 month, 2 months, 3 months, 6 months, 1 year or more. The vaccine vector may comprise viable microorganisms prior to administration, but in some embodiments the vector may be killed prior to administration. In some embodiments, the vector may be able to replicate in the subject, while in other embodiments the vector may not be capable of replicating in the subject, e.g. a killed vaccine vector or a liposome. Methods of inactivating microorganisms used as vectors are known to those of skill in the art. For example, a bacterial vaccine vector may be inactivated using formalin, ethanol, heat exposure, or antibiotics. Those of skill in the art may use other methods as well.

It is envisioned that several epitopes or antigens from the same or different pathogens may be administered in combination in a single vaccine to generate an enhanced immune response against multiple antigens. Recombinant vaccines may encode antigens from multiple pathogenic microorganisms, viruses or tumor associated antigens. Administration of vaccine capable of expressing multiple antigens has the advantage of inducing immunity against two or more diseases at the same time. For example, live attenuated bacteria provide a suitable vector for eliciting an immune response against multiple antigens from a single pathogen, e.g., FliC and PAL from *Salmonella* or against multiple antigens from different pathogens, e.g., Influenza and *Salmonella*.

Vaccine vectors may be constructed using exogenous polynucleotides encoding antigens which may be inserted into the vaccine vector at any non-essential site or alternatively may be carried on a plasmid or other extra chromosomal vehicle (e.g. a BAC or YAC) using methods well known in the art. One suitable site for insertion of polynucleotides is within external portions of transmembrane proteins or coupled to sequences that target the exogenous polynucleotide for secretory pathways and/or allow attachment to the cell wall. One example of a suitable transmembrane protein for insertion of polynucleotides is the lamB gene. One suitable method of cell wall attachment is provided in the Examples Exogenous polynucleotides include, but are not limited to, polynucleotides encoding antigens selected from pathogenic microorganisms or viruses and include polynucleotides that are expressed in such a way that an effective immune response is generated. Such polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Exogenous polynucleotides can also be obtained from pathogenic bacteria, e.g., genes encoding bacterial proteins such as toxins, outer membrane proteins or other highly conserved proteins. Further, exogenous polynucleotides from parasites, such as Apicomplexan parasites are attractive candidates for use in a vector vaccine.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements. The terms "a", "an" and "the" may mean one or more than one unless specifically delineated.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

The following examples are meant only to be illustrative and are not meant as limitations on the scope of the invention or of the appended claims. All references, included patents, patent publications and non-patent literature, cited herein are hereby incorporated by reference in their entirety. Any conflict between statements in references and those made herein should be resolved in favor of the statements contained herein.

Examples

We selected the Pal polypeptide from *E. coli* as a highly conserved polypeptide that may include a polypeptide that would be both highly conserved among the gram-negative pathogenic bacteria and immunogenic. We began by selecting the *E. coli* sequence from amino acid 106-124 of Pal (P0A912). The antigenic potential of the selected sequence was confirmed using the Network Protein Sequence Analysis program against published sequences found in EMBL and NCBI databases (Combet, C., C. Blanchet, C. Geourjon, and G. Deleage. 2000. NPS@: network protein sequence analysis. Trends Biochem Sci 25:147-50). The sequence was then used to search for sequence homology using a Blast search engine on Swiss Institute of Bioinformatics on the EXPASY server. The Blast search found a number of proteins (Pal) with identical sequences to our initially selected Pal sequence (TVEGHADERGTPEYNISLG (SEQ ID NO: 8)). The list of Pal proteins with identical sequence include *E. coli* spp, *Salmonella typhi* and *paratyphi* spp, *Shigella* spp, *Enterobacter* spp, *Citrobacter* spp, *Cronobacter* spp. Also, Pal proteins with greater than 94% homology (only one amino acid different with or without similar substitution of a second amino acid) are *Vibrio* spp, *Sodalis* spp, *Erwinia* spp, *Klebsiella* spp, *Dickeya* spp, *Serratia* spp, *Proteus* spp, *Xenorhabdus* spp, *Pectobacterium* spp, and *Pantoea* spp with 100% coverage.

To optimize the antigen for other pathogen species, the 17th amino acid will be changed from serine to alanine. The new sequence would be TVEGHADERGTPEYNIALG (SEQ ID NO: 32). This sequence is expected to provide optimal immune stimulation for *Vibrio* spp, *Sodalis* spp, *Erwinia* spp, *Klebsiella* spp, *Dickeya* spp, *Serratia* spp, *Proteus* spp, *Xenorhabdus* spp, *Pectobacterium* spp, and *Pantoea* spp with 100% coverage and either identical or similar amino acid sequence. The proteins of these species would be expected to be targeted by the immune system following vaccination and provide protection against these organisms.

The PAL epitope (TVEGHADERGTPEYNISLG (SEQ ID NO: 8)) was inserted into a *Bacillus subtilis* (BS) vector and expressed. The PAL *Bacillus* construct was then tested as a vaccine vector for *Salmonella* by vaccinating chicks via oral gavage with $10^8$ cfu/chick on the day of hatch and comparing to chicks treated similarly with the *Bacillus* backbone (BS BB) or saline. The birds were boosted with the same treatment at 11 days post-hatch. Samples were harvested for specific immune response on day 17. The immune response to the vaccine was evaluated by measuring serum IgG (FIG. 1) and secretory ileal IgA (FIG. 2). Following vaccination with the selected sequence of Pal expressed on the *Bacillus* there was a significant serum and secretory immune response specifically against the Pal sequence compared to controls (FIGS. 1 and 2).

Evaluation of potential *Bacillus* vectored vaccine candidates against *Salmonella typhimurium* (ST) challenge at 11 days post-vaccination was undertaken by enumerating *Salmonella* colonies in the ceca of vaccinated chickens at day 17 and 21 post-hatch (or day 6 and 10 after challenge). The levels of ST in the ceca were measured using conventional microbiological techniques. Chickens that were vaccinated with the selected sequence of Pal expressed on the *Bacillus* vector had significantly decreased levels of *Salmonella* in the ceca. As shown in FIG. 3, the level of *Salmonella* in the ceca was decreased by over 41/2 logs in chicks vaccinated with BS-PAL (BSNNP) as compared to chicks vaccinate with saline or the BS BB. This is the first effective vaccine against *Salmonella* that is vectored by a Generally Recognized As Safe (GRAS) organism by the Food and Drug Administration (FDA) such as *Bacillus subtilis.*

In an investigation aimed at optimization of the immunogen sequence, referred to as PAL above (TVEGHADERGTPEYNISLG (SEQ ID NO: 8)), an epitope mapping experiment was designed to assess the relative antigenicity of portions of this 19-mer oligopeptide PAL. The sequence was split into 7 hexapeptides that overlapped by 3 amino acids each. For example, TVEGHA (SEQ ID NO: 39), GHADER (SEQ ID NO: 2), and DERGTP (SEQ ID NO: 3) each share three amino acids with the portion of sequence immediately to the left (toward the amino terminus) and right (toward the carboxy terminus). For this purpose, seven hexapeptides straddling amino acid residues 1-3, 4-6, 7-9 etc. were synthesized and coupled to bovine serum albumin (BSA). Two monoclonal antibodies (mAbs, designated 2B5 and 1B2) that reacted strongly with both the PAL 19-mer peptide and the native epitope as displayed on the cell wall of *Salmonella* (and related species) were selected and their relative affinities towards each segment of PAL were tested (FIG. 4).

The results indicated that, out of the 7 peptides tested, PAL1 (3 residues pre-PAL, "YKV", and PAL amino terminal residues "TVE"; SEQ ID NO: 38) was the least antigenic for both mAbs. This can be explained by the observation that threonine is an uncharged amino acid and valine is an aliphatic residue, both of which are relatively hydrophobic and thus less likely to be accessible in the original immunogen PAL. Less accessible residues are unlikely to induce a potent immune response. In addition, most antibody epitopes are hydrophilic in nature. In contrast, the two best reacting mAbs had a much higher affinity for PAL6 (SEQ ID NO: 4) and PAL7 (SEQ ID NO: 6) (ELISA absorption levels compared to PAL1 were twice as high for PAL6 and >50% higher for PAL7). These results clearly indicate that the C-terminal half of PAL was likely the more exposed and accessible part of the immunogen and the most crucial portion of the immunogen with regard to generation of an antibody population that strongly cross-reacted with the native protein as displayed by *Salmonella* and related bacterial species. Interestingly, in order to generate the PAL7 hexapeptide, 2 residues were added that were not part of the original 19-mer PAL, but that flank PAL in the native bacterial protein: E (glutamate) and R (arginine). Both of these are charged residues and hence have a high probability of being exposed in our bacterial target species.

Based on the above rationale, a new 19-mer, designated PALbis (SEQ ID NO: 1), was generated. PALbis is different from the original PAL 19-mer in that (1) it no longer contains the two N-terminal amino acids T (threonine) and V (valine) and (2) it has been extended C-terminally with two additional residues, i.e. E (glutamate) and R (arginine). Thus, the improved amino acid sequence, PALbis, is EGHADERGTPEYNISLGER (SEQ ID NO: 1). PALbis was compared against multiple genera of bacteria to ensure cross-species reactivity was maintained (BLAST results are shown in Table 1). Sequence homology among *E. coli, Salmonella typhi* and *paratyphi, Shigella, Enterobacter, Citrobacter*, and *Cronobacter* spp. still had 100% homology. Sequence homology among *Vibrio, Sodalis, Erwinia, Klebsiella, Dickeya, Serratia, Proteus, Xenorhabdus, Pectobacterium*, and *Pantoea* spp. have 95% homology with a single amino acid substitution S15A (SEQ ID NO: 6). The related *Campylobacter jejuni* sequence is shown as SEQ ID NO: 7 and has 65% identity with the sequence of SEQ ID NO: 1. Thus we choose to pursue vaccine vectors expressing SEQ ID NO: 1 to obtain cross-strain immune responses with a single vaccine vector.

TABLE 1

Sequence comparison of PALbis (SEQ ID NO: 1) among bacteria

| | |
|---|---|
| PALbis Sequence:<br>EGHADERGTPEYNISLGER | *E. coli* (SEQ ID NO: 1) |
| EGHADERGTPEYNIALGER | *Vibrio* (SEQ ID NO: 6) |
| EGNCDEWGTDEYNQALG_ | *Campylobacter* (SEQ ID NO: 7) |

| Bacteria | Homology (%) |
|---|---|
| *Escherichia coli* | 100 |
| *Salmonella enteriditis* | 100 |
| *Salmonella typhimurium* | 100 |
| *Salmonella choleraesuis* | 100 |
| *Salmonella enterica* subspecies Montevideo | 100 |
| *Salmonella enterica* subspecies Kentucky | 100 |
| *Shigella flexneri* | 100 |
| *Shigella dysenteriae* | 100 |
| *Enterobacter radicincitans* | 100 |
| *Enterobacter hormaechei* | 100 |
| *Enterobacter asburiae* | 100 |
| *Enterobacter cancerogenus* | 100 |
| *Enterobacter cloacae* | 100 |
| *Enterobacter aerogenes* | 95 |
| *Citrobacter koseri* | 100 |
| *Citrobacter freundii* | 100 |
| *Citrobacter rodentium* | 100 |
| *Citrobacter youngae* | 100 |
| *Vibrio cholera* | 95 |

TABLE 1-continued

Sequence comparison of PALbis (SEQ ID NO: 1) among bacteria

| | |
|---|---|
| Vibrio scophthalmi | 95 |
| Vibrio rotiferianus | 95 |
| Vibrio ichthyoenteri | 95 |
| Vibrio harceyi | 95 |
| Vibrio mimicus | 95 |
| Vibrio alginolyticus | 95 |
| Vibrio shilonii | 95 |
| Vibrio parahaemolyticus | 95 |
| Vibrio tubiashii | 95 |
| Vibrio sinaloensis | 95 |
| Vibrio brasiliesis | 95 |
| Vibrio caribbenthicus | 95 |
| Vibrio orientalis | 95 |
| Vibrio ordalii | 95 |
| Vibrio nigripulchritudo | 95 |
| Vibrio anguillarum | 95 |
| Vibrio furnissii | 95 |
| Vibrio metschnikovii | 95 |
| Vibrio coralliilyticus | 95 |
| Vibrio splendidus | 95 |
| Vibrio vulnificus | 95 |
| Cronobacter sakazakii | 100 |
| Sodalis glossinidius | 95 |
| Erwinia billingiae | 95 |
| Klebsiella oxytoca | 95 |
| Klebsiella pneumonia | 95 |
| Dickeya dadantii | 95 |
| Dickeya zeae | 95 |
| Serratia symbiotica | 95 |
| Serratia plymuthica | 95 |
| Serratia proteamaculans | 95 |
| Serratia odorifera | 95 |
| Proteus mirabilis | 95 |
| Proteus penneri | 95 |
| Xenorhabdus bovienii | 95 |
| Xenorhabdus nematophila | 95 |
| Pectobacterium wasabiae | 95 |
| Pectobacterium carotovorum | 95 |
| Pectobacerium atrosepticum | 95 |
| Pantoea stewartii | 95 |
| Pantoea ananatis | 95 |
| Campylobacter jejuni | 65 |

Figure 5:
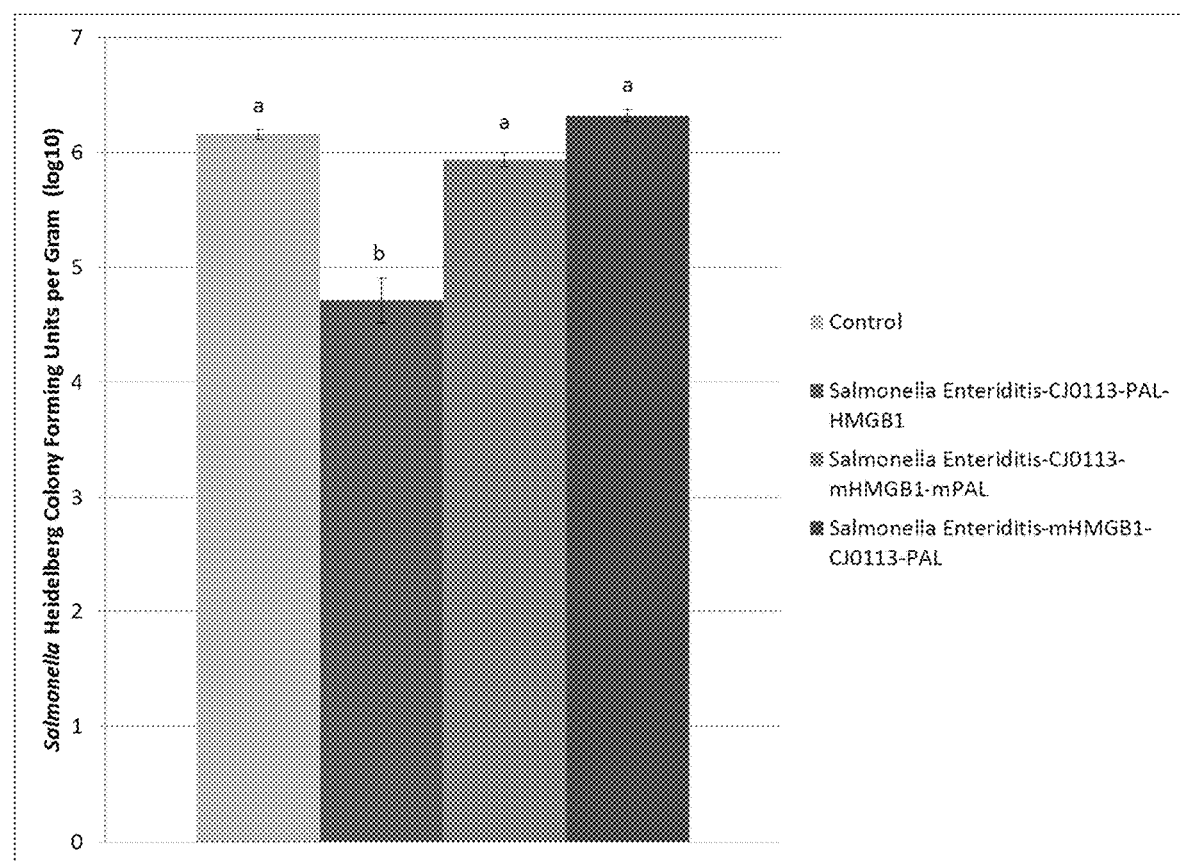
FIG. 5 is a graph showing the *Salmonella Heidelberg* colony forming units (cfu) per gram isolated from the ceca of 21-day-old broilers after vaccination with the indicated vaccine strain or control. Groups with different upper case letters are significantly different by ANOVA (P<0.05).

To test the ability of PALbis (SEQ ID NO: 1) to work in a cross-strain challenge experiment, several vaccine candidates were generated. The vaccine vectors used herein were generated substantially as described in International Publication No. WO2008/036675 and International Publication No. WO2011/091255. Three separate constructs were generated and incorporated into two separate vaccine vectors, either *Salmonella Enteriditis* or *Salmonella Typhimurium*. The inserts used included a polynucleotide encoding the CJ0113 epitope described as SEQ ID NO: 31 herein and originally described in International Publication No. WO2011/156619, a polynucleotide encoding the HMGB1 polypeptide of SEQ ID NO: 24 which was originally described in International Publication No. WO2011/091255, and the PALbis sequence of SEQ ID NO: 1 identified and described herein. The three polynucleotides were separated by serine spacers (three serine residues inserted to avoid steric hindrance issues) and inserted in various orders in frame into external loop 9 of the *Salmonella* transmembrane protein lamB. The resulting nucleic acid and amino acid sequences of the inserts are shown in SEQ ID NO: 41-46. SEQ ID NO: 41 and 42 are the nucleic acid and amino acid sequences of the CJ0113-PAL-HMGB1 insert, respectively. SEQ ID NO: 43 and 44 are the nucleic acid and amino acid sequences of the CJ0113-HMGB1-PAL insert, respectively. SEQ ID NO: 45 and 46 are the nucleic acid and amino acid sequences of the HMGB1-CJ0113-PAL insert, respectively. The purpose of generating three vaccine vectors with the same inserts in a variety of orders was to control for any position or steric hindrance effects of the polypeptides interacting with unmapped surface moieties on the vector agents which could make the HMGB1 binding domain inaccessible to receptors on the host cells, or which might make surface-presented antigens inaccessible to the host immune cells.

*Salmonella Enteriditis* vectored vaccines reduced *Salmonella Heidelberg* recovery after challenge. Chicks were vaccinated with a *Salmonella Enteriditis* vectored vaccine that belongs to a heterologous *Salmonella* serogroup when compared to the *Salmonella Heidelberg* challenge strain to determine whether the PAL antigen would generate a cross *Salmonella* serogroup immune response. Live *Salmonella Enteriditis*-CJ0113-PAL-HMGB1, live *Salmonella Enteriditis*-CJ0113-HMGB1-PAL (which was later determined to contain two point mutations in HMGB1 and a frame-shift mutation in PAL resulting in the PAL epitope of SEQ ID NO: 35), and live *Salmonella Enteriditis*-HMGB1-CJ0113-PAL (with a later determined point mutation in HMGB1) vaccines were oral gavaged in 1-day-old chicks at $4\times10^8$ cfu/chick. Chicks were challenged on day 7 with a *Salmonella Heidelberg* at $7\times10^6$ cfu/chick by oral gavage. *Salmonella Heidelberg* colony forming units (cfu) per gram isolated from the ceca of 21-day-old broiler chick were determined. *Salmonella Heidelberg* cfu/g that were recovered from the ceca 14 days after challenge of live *Salmonella*

Enteriditis-CJ0113-PAL-HMGB1 vaccinated chickens were significantly lower than from live Salmonella Enteriditis-CJ0113-HMGB1-PAL with two point mutations in HMGB1 and a frame-shift mutation in PAL vaccinated chickens, live Salmonella Enteriditis-HMGB1-CJ0113-PAL with a point mutation in HMGB1 vaccinated chickens, and non-vaccinated control chickens (FIG. 5; P=0.003).

Figure 6:
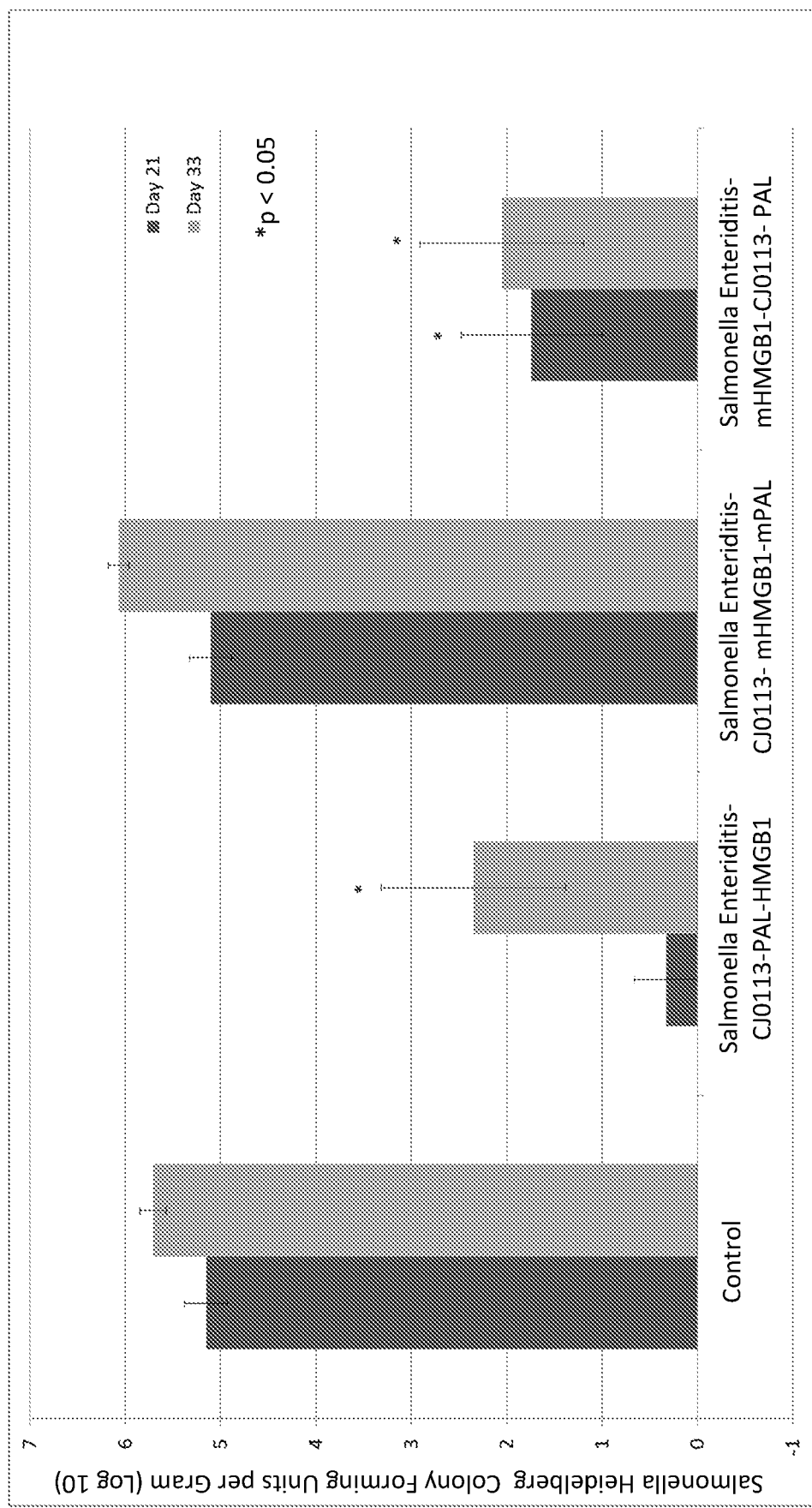
FIG. 6 is a graph showing the *Salmonella Heidelberg* colony forming units (cfu) per gram isolated from the ceca of 21-day-old and from 33-day-old broilers after vaccination with the indicated vaccine strain or control (From left to right the graph shows control vaccinated chickens at 21 and 33 days after challenge, or chickens vaccinated with *Salmonella enteriditis* with the inserts arranged from N to C terminal as CJ0113-PAL-HMGB1; CJ0113-mHMGB1-mPAL or mHMGB1-CJ0113-PAL, wherein m is an indication of a mutation in the sequence of the protein). Groups with an asterisk are significantly different by ANOVA ($P<0.05$).

Chicks were also vaccinated with glutaraldehyde-inactivated Salmonella Enteriditis vectored vaccines belonging to a heterologous Salmonella serogroup when compared to the Salmonella Heidelberg challenge to determine whether the PAL antigen would generate a cross Salmonella serogroup immune response. Glutaraldehyde-inactivated Salmonella Enteriditis-CJ0113-PAL-HMGB1, Salmonella Enteriditis-CJ0113-mHMGB1-mPAL (with point mutations in HMGB1 and a frameshift mutation in PAL), Salmonella Enteriditis-mHMGB1-CJ0113-PAL (with a point mutation in HMGB1) vaccines were adjuvated with mannosylated chitosan (as described in International Application No. PCT/US13/67212). The prepared vaccines were used to oral gavage 1-day-old chicks at 1×10$^9$ cfu/chick. Chicks were challenged on day 17 with a Salmonella Heidelberg at 8.5×10$^6$ cfu/chick by oral gavage. Glutaraldehyde-inactivated Salmonella Enteriditis-CJ0113-PAL-HMGB1 vaccination and Salmonella Enteriditis-mHMGB1-CJ0113-PAL vaccination in broilers significantly reduced Salmonella Heidelberg recovery from the ceca five days after challenge (FIG. 6; P<0.05), and Salmonella Heidelberg recovery remained low in Salmonella Enteriditis-mHMGB1-CJ0113-PAL and Salmonella Enteriditis-CJ0113-PAL-HMGB1 vaccinated chickens seventeen days after challenge (P=0.033). These data indicate that the PAL epitope in these vaccines provided protection against a cross-serogroup Salmonella challenge considering that the vaccine backbone originated from a Salmonella serogroup D strain and protected against a Salmonella serogroup B challenge.

Figure 4:
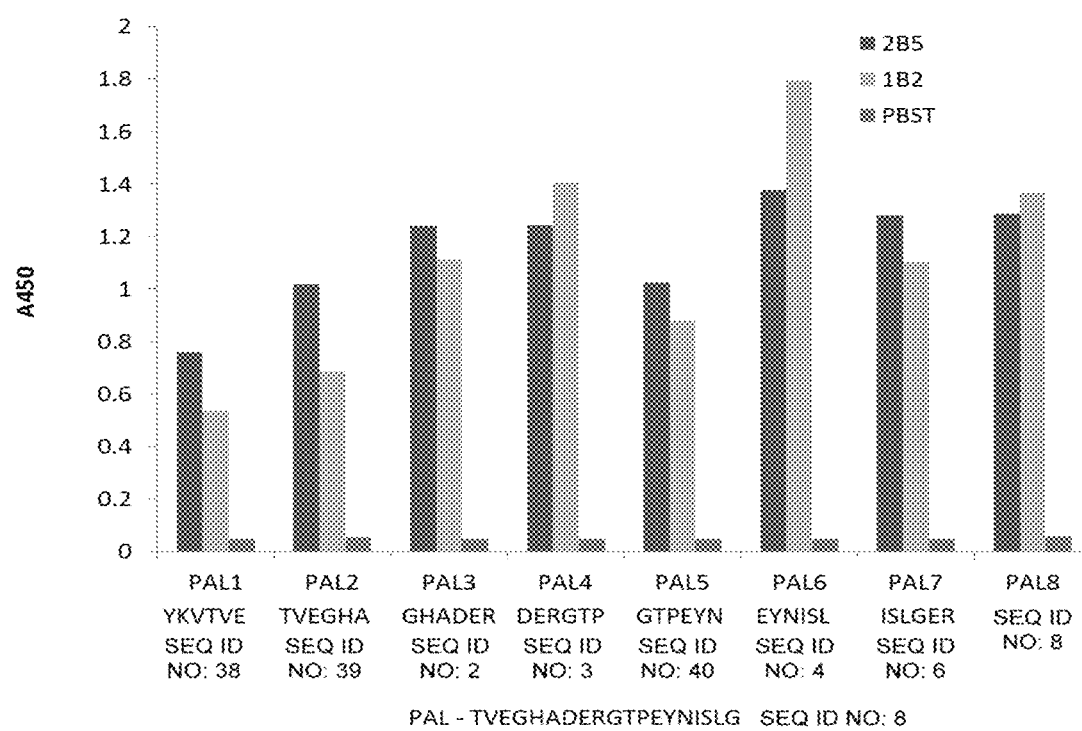
FIG. 4 is a graph showing the affinity of two monoclonal antibodies (2B5 and 1B2) as compared to control (PBST) for the indicated hexapeptides of PAL.

Notably, these experiments were not useful to determine if there was any effect of the relative orientation or position of the three polypeptides in the vaccine vector because there were mutations discovered in the inserts. The mutations were informative regarding the protective or immunogenic portion of the PAL polypeptide. A single nucleotide deletion was found in the PAL polynucleotide of the Salmonella Enteriditis-CJ0113-mHMGB1-mPAL vaccine. The wild-type PAL nucleotide sequence is 5'-GAAGGTCACGCG-GACGAACGTGGTACCCCGGAATA-CAACATCTCTCTGGGTGAA CGT-3' (SEQ ID NO: 33; the guanine deleted in the mutant sequence is underlined) and the mutant PAL sequence found in the Salmonella Enteriditis-CJ0113-mHMGB1-mPAL is 5'-GAAGGT-CACGCGGACGAACGTGGTACCCCGAATA-CAACATCTCTCTGGGTGAAC GT-3' (SEQ ID NO: 34). The guanine deletion (underlined in the wild-type sequence) 31 base pairs into the PAL nucleotide sequence caused a frame-shift mutation that changed the last eight amino acids of the PAL peptide sequence. The wild-type PAL of SEQ ID NO: 1 becomes SEQ ID NO: 35 (EGHADERGTPNTT-SLWVN; the last eight amino acids are underlined and are different than those found in SEQ ID NO: 1). The lack of development of an effective immune response by this mutant PAL is likely due to the loss of the last nine amino acids of PAL, which were shown to be important for development of an antibody response in FIG. 4 above. Thus a minimal PAL epitope may be SEQ ID NO: 36 (EYNISLGER) or its Vibrio counterpart SEQ ID NO: 37 (EYNIALGER).

Figure 7:
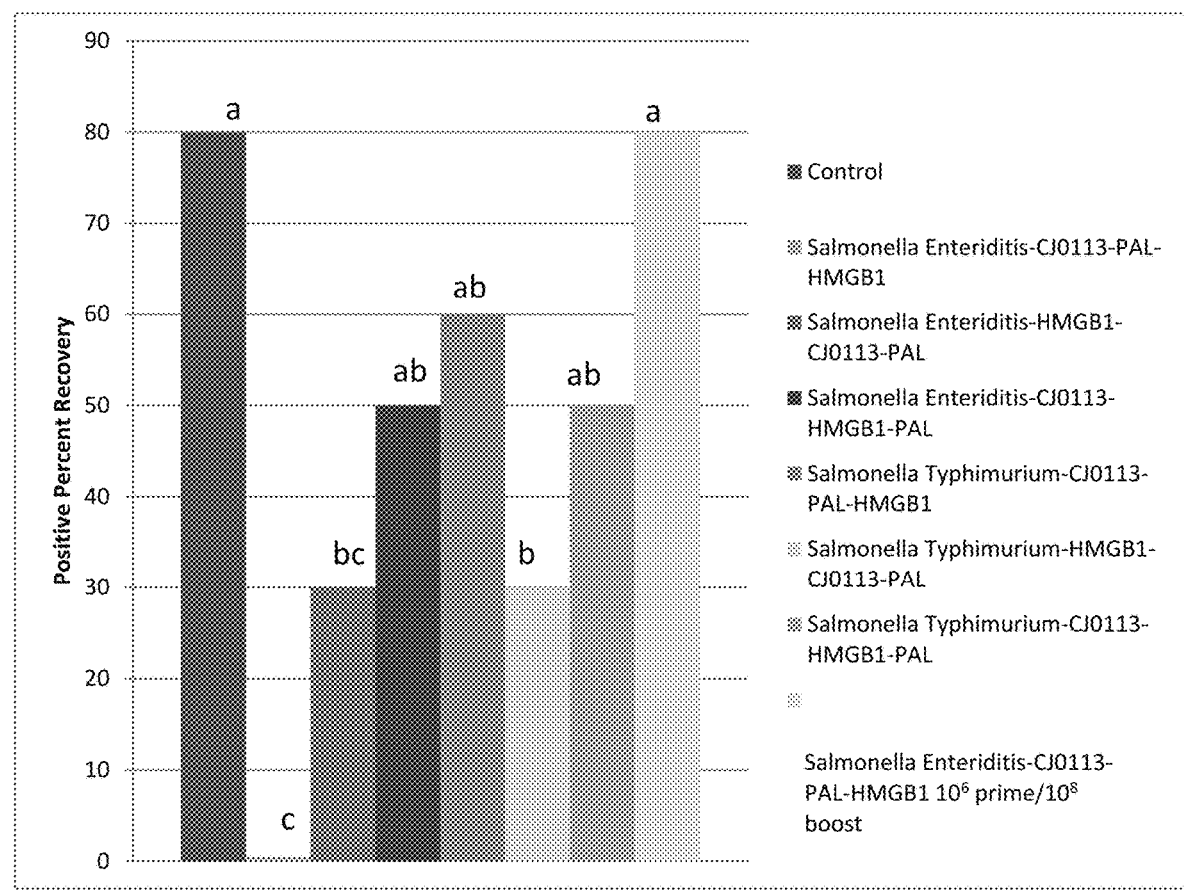
FIG. 7 is a graph showing the *Salmonella Heidelberg* positive percent recovery from the ceca of 28 day old broilers after vaccination with the indicated vaccine strain or controls. Groups with different upper case letters are significantly different by ANOVA ($P<0.05$).

The vaccines were remade to correct the mutations noted above. Once the mutations were corrected, live Salmonella Enteriditis-CJ0113-PAL-HMGB1, live Salmonella Enteriditis-HMGB1-CJ0113-PAL, and live Salmonella Typhimurium-HMGB1-CJ0113-PAL vaccination in broilers significantly reduced Salmonella Heidelberg recovery after enrichment with tetrathionate for 24 hours from broilers' ceca collected 10 days after challenge (FIG. 7; P<0.05). Day of hatch chicks were vaccinated with 10$^7$ cfu of live-Salmonella Enteriditis-CJ0113-PAL-HMGB1, Salmonella Enteriditis-CJ0113-HMGB1-PAL, Salmonella Enteriditis-HMGB1-CJ0113-PAL, Salmonella Typhimurium-CJ0113-PAL-HMGB1, Salmonella Typhimurium-CJ0113-HMGB1-PAL, or Salmonella Typhimurium-HMGB1-CJ0113-PAL by oral gavage. An additional group of day of hatch chicks was vaccinated with 10$^6$ cfu Salmonella Enteriditis-CJ0113-PAL-HMGB1 by oral gavage. Salmonella Enteriditis-CJ0113-PAL-HMGB1, Salmonella Enteriditis-CJ0113-HMGB1-PAL, Salmonella Enteriditis-HMGB1-CJ0113-PAL, Salmonella Typhimurium-CJ0113-PAL-HMGB1, Salmonella Typhimurium-CJ0113-HMGB1-PAL, or Salmonella Typhimurium-HMGB1-CJ0113-PAL vaccinated chickens were boosted at 14-days-old with 10$^7$ cfu of the respective vaccine. Salmonella Enteriditis-CJ0113-PAL-HMGB1 vaccinated chickens that received 10$^6$ cfu on day of hatch were boosted with 10$^8$ cfu of Salmonella Enteriditis-CJ0113-PAL-HMGB1. Chickens were challenged on day 17 with 6×10$^6$ cfu/chicken by oral gavage and the results are shown in FIG. 7 as percent challenge bacteria recovery. The results suggest that the position of each of the insert in the vaccine vector may affect the level of protection offered by the vaccine.

Figure 8:
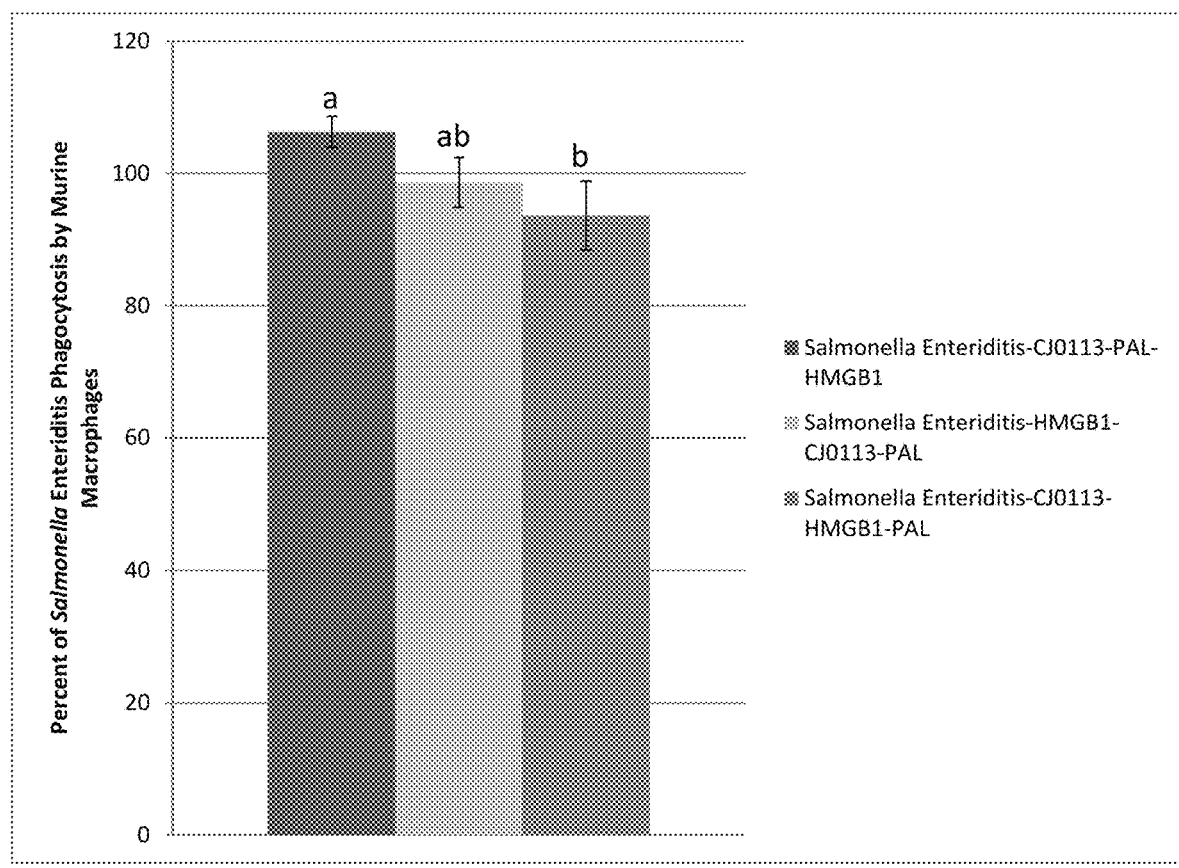
FIG. 8 is a graph showing the percent phagocytosis of the indicated vaccine strains by murine macrophages. Groups with different upper case letters are significantly different by ANOVA ($P<0.05$).

PAL expression on the Salmonella Enteriditis bacterial cell surface will directly interact with B lymphocytes to stimulate antibody production. HMGB1 expression on the Salmonella Enteriditis cell surface affects the percentage phagocytic uptake into murine macrophages (FIG. 8). Murine macrophages from the Raw 264 cell line were co-cultured with live Salmonella Enteriditis vaccine vector, Salmonella Enteriditis-CJ0113-PAL-HMGB1, Salmonella Enteriditis-CJ0113-HMGB1-PAL, or Salmonella Enteriditis-HMGB1-CJ0113-PAL for one hour. Escherichia coli pHrodo red bioparticles were added to each culture and incubated for two hours. After the bioparticles and bacteria are engulfed by the macrophage a phagosome is created. The phagosome fuses with a lysosome fuses acidifying the inside of the phagolysosome. The fluorescence intensity of the bioparticles increase as the pH becomes more acidic; therefore, the bioparticles within a phagolysosome will have higher fluorescence intensity. Salmonella Enteriditis-CJ0113-PAL-HMGB1 percentage phagocytic uptake was higher than Salmonella Enteriditis-HMGB1-CJ0113-PAL which was higher than Salmonella Enteriditis-CJ0113-HMGB1-PAL suggesting that HMGB1 at the end of the insert interacts favorably with the cell surface and enhances phagocytic uptake.

Based on these data, the linear display of chimeric DNA alters protein folding that is dependent upon the position of charged amino acids. Different linear combinations of antigens and immune stimulatory molecules will affect the spatial arrangement of each antigen and immune stimulatory on the bacterial cell surface. The protein expression of these linear combinations may differ for each bacteria species because the channel proteins on the bacteria cell surface creating steric hindrance with surrounding channel proteins. Reduced vaccine efficacy could be the result of unfavorable PAL or HMGB1 protein expression due to steric hindrance.

We claim:

1. A vaccine vector comprising a first polynucleotide encoding a first antigenic polypeptide consisting of a PAL polypeptide selected from the group consisting of SEQ ID NO: 2, SEQ ID NO: 3, SEQ ID NO: 4, SEQ ID NO: 5, SEQ ID NO: 6, SEQ ID NO: 8, SEQ ID NO: 32, SEQ ID NO: 36, SEQ ID NO: 37 and combinations thereof, wherein the PAL polypeptide is expressed on the surface of the vaccine vector.

2. The vaccine vector of claim 1, further comprising a second polynucleotide encoding an immunostimulatory polypeptide consisting of an HMGB1 polypeptide selected from the group consisting of SEQ ID NOs: 15-23 and combinations thereof, wherein the HMGB1 polypeptide is expressed on the surface of the vaccine vector.

3. The vaccine vector of claim 2, wherein the vector comprises more than one copy of the first polynucleotide and/or more than one copy of the second polynucleotide.

4. The vaccine vector of claim 2, wherein the first polynucleotide is linked in frame to the second polynucleotide.

5. The vaccine vector of claim 4, wherein the first polynucleotide and the second polynucleotide are linked via a spacer nucleotide.

6. The vaccine vector of claim 1, wherein the vector is selected from the group consisting of a virus, a bacterium, a yeast and a liposome.

7. The vaccine vector of claim 6, wherein the vaccine vector is selected from the group consisting of *Bacillus* spp., *Salmonella* spp., *Lactobacillus* spp., and *Escherichia* spp.

8. The vaccine vector of claim 2, further comprising a third polynucleotide encoding a second antigenic polypeptide.

9. The vaccine vector of claim 8, wherein the second antigenic polypeptide is a polypeptide selected from SEQ ID NO: 7 or SEQ ID NO: 31.

10. A pharmaceutical composition comprising the vaccine vector of claim 1 and a pharmaceutically acceptable carrier.

11. A method of enhancing the immune response against a gram-negative bacterium in a subject comprising administering to the subject the vaccine vector of claim 1 in an amount effective to enhance the immune response of the subject to the gram-negative bacterium.

12. The method of claim 11, wherein the enhanced immune response comprises an enhanced antibody response, an enhanced T cell response or both.

13. A method of reducing morbidity associated with infection with a gram-negative bacterium in a subject comprising administering to the subject the vaccine vector of claim 1 in an amount effective to reduce the morbidity associated with subsequent infection of the subject with a gram-negative bacterium as compared to a control subject not administered the vaccine vector.

14. The method of claim 11, wherein the vaccine vector is administered by a route selected from the group consisting of oral, mucosal, parenteral, sub-cutaneous, intramuscular, intraocular and in ovo.

15. The method of claim 11, wherein the subject is selected from the group consisting of a poultry species and a mammal.

16. The method of claim 15, wherein the subject is selected from the group consisting of a human, a chicken and a turkey.

17. The method of claim 11, wherein from about $10^4$ to about $10^9$ vector copies of the vaccine are administered to the subject.

18. The method claim 11, wherein the vaccine vector is killed prior to administration to the subject or is not capable of replicating in the subject.

19. The method of claim 11, wherein the gram-negative bacterium is selected from the group consisting of *Salmonella* spp, *Escherichia* spp, *Shigella* spp, *Vibrio* spp, *Erwinia* spp, *Klebsiella* spp, *Citrobacter* spp, *Yersinia* spp, and *Providencia* spp.

* * * * *